(12) United States Patent
Ng et al.

(10) Patent No.: US 11,844,941 B2
(45) Date of Patent: Dec. 19, 2023

(54) SELF-EXPANDING NERVE CUFF ELECTRODE

(71) Applicant: THE ALFRED E. MANN FOUNDATION FOR SCIENTIFIC RESEARCH, Valencia, CA (US)

(72) Inventors: Boon Khai Ng, La Crescenta, CA (US); William Alexander Dai, Ventura, CA (US)

(73) Assignee: THE ALFRED E. MANN FOUNDATION SCIENTIFIC RESEARCH, Valencia, CA (US)

( * ) Notice: Subject to any disclaimer, the term of this patent is extended or adjusted under 35 U.S.C. 154(b) by 69 days.

(21) Appl. No.: 17/206,087

(22) Filed: Mar. 18, 2021

(65) Prior Publication Data

US 2021/0205614 A1 Jul. 8, 2021

Related U.S. Application Data

(63) Continuation of application No. 15/967,468, filed on Apr. 30, 2018, now Pat. No. 10,981,000.

(60) Provisional application No. 62/500,080, filed on May 2, 2017, provisional application No. 62/500,091, filed on May 2, 2017.

(51) Int. Cl.
*A61N 1/05* (2006.01)
*A61B 5/00* (2006.01)
*A61B 5/24* (2021.01)
*A61B 5/296* (2021.01)

(52) U.S. Cl.
CPC .......... *A61N 1/0556* (2013.01); *A61B 5/4818* (2013.01); *A61N 1/0558* (2013.01); *A61B 5/24* (2021.01); *A61B 5/296* (2021.01); *A61B 5/686* (2013.01); *A61B 5/6877* (2013.01); *A61B 2562/0209* (2013.01)

(58) Field of Classification Search
None
See application file for complete search history.

(56) References Cited

U.S. PATENT DOCUMENTS 6,600,956 B2 * 7/2003 Maschino ............ A61N 1/0556
607/118
2003/0040785 A1 * 2/2003 Maschino ............ A61N 1/0556
607/118

(Continued)

*Primary Examiner* — Erica S Lee
(74) *Attorney, Agent, or Firm* — Michael J. Bolan; VISTA IP LAW GROUP, LLP

(57) ABSTRACT

An electrode lead comprises an elongated lead body, at least one lead connector terminal affixed to the proximal end of the lead body, and an electrically insulative cuff body affixed to the distal end of the lead body. The cuff body is configured for being circumferentially disposed around a nerve. The cuff body comprises cutouts, slits, a wrinkled portion, a thin stretchable portion, and/or a serpentine strap, which increases that increase the expandability of the cuff body when disposed around the nerve. The electrode lead further comprises at least one electrode contact affixed to the cuff body, and at least one electrical conductor extending through the lead body between the at least one lead connector terminal and the electrode contact(s). If the cuff body comprises cutouts or slits, the electrode lead can further comprise a thin stretchable film affixed to the cuff body over cutouts or slits.

9 Claims, 33 Drawing Sheets

(56) References Cited

U.S. PATENT DOCUMENTS

| | | | |
|---|---|---|---|
| 2009/0210042 A1* | 8/2009 | Kowalczewski | A61B 5/4041 600/377 |
| 2014/0228905 A1* | 8/2014 | Bolea | A61N 1/3615 607/42 |
| 2021/0205622 A1* | 7/2021 | Lu | A61B 5/24 |

* cited by examiner

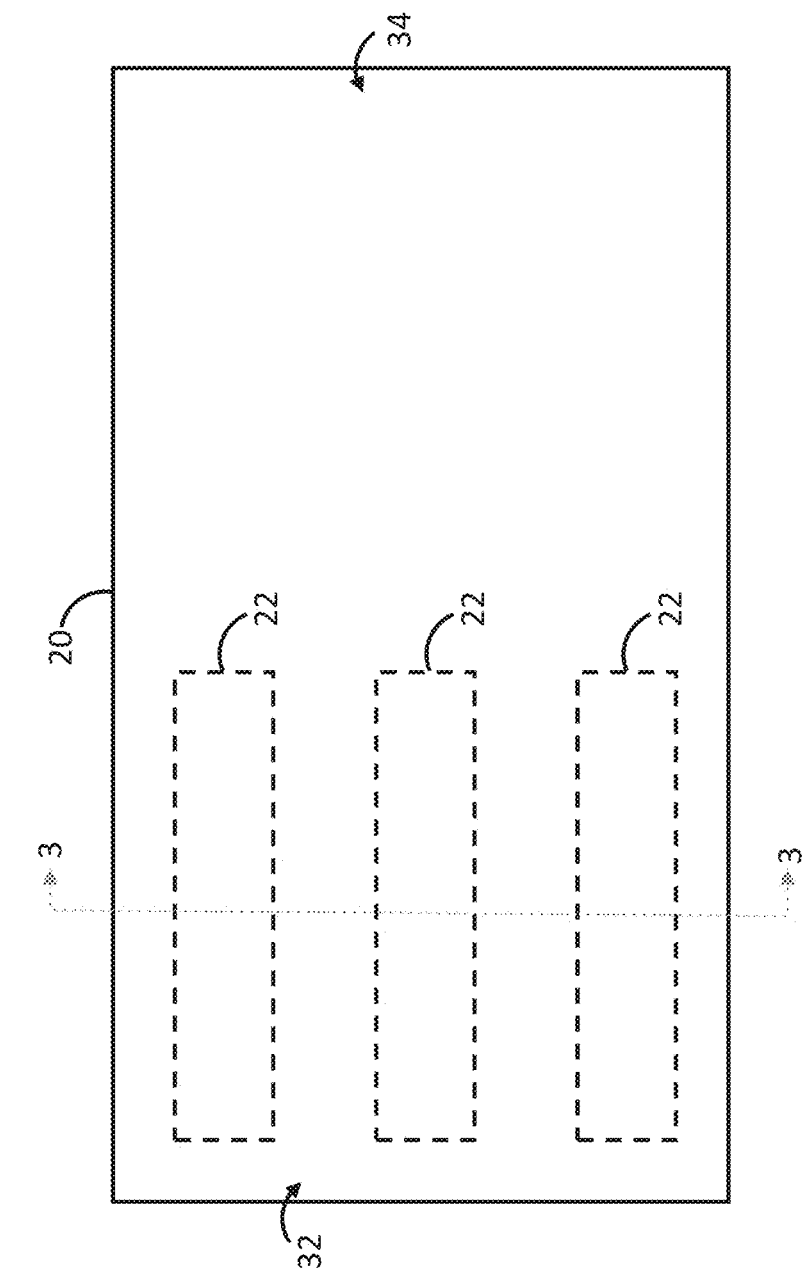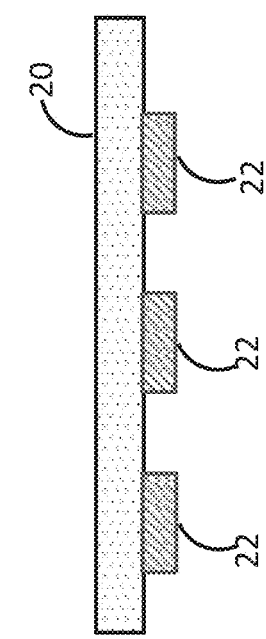

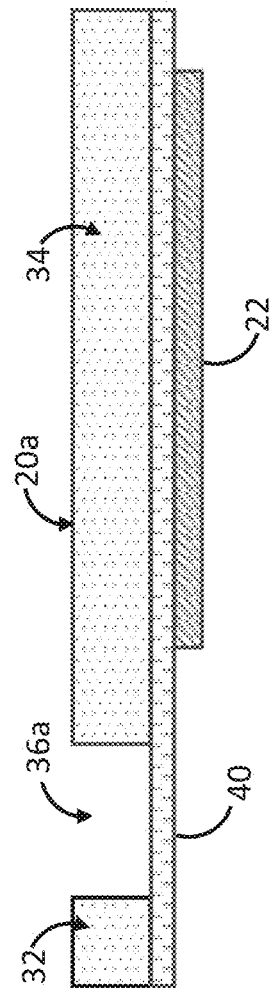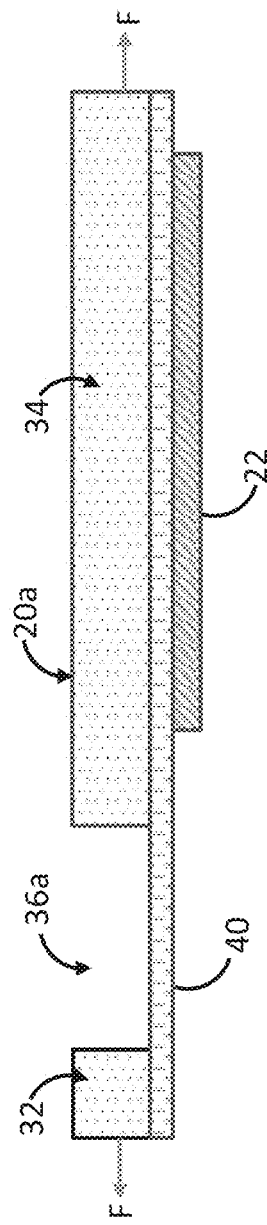

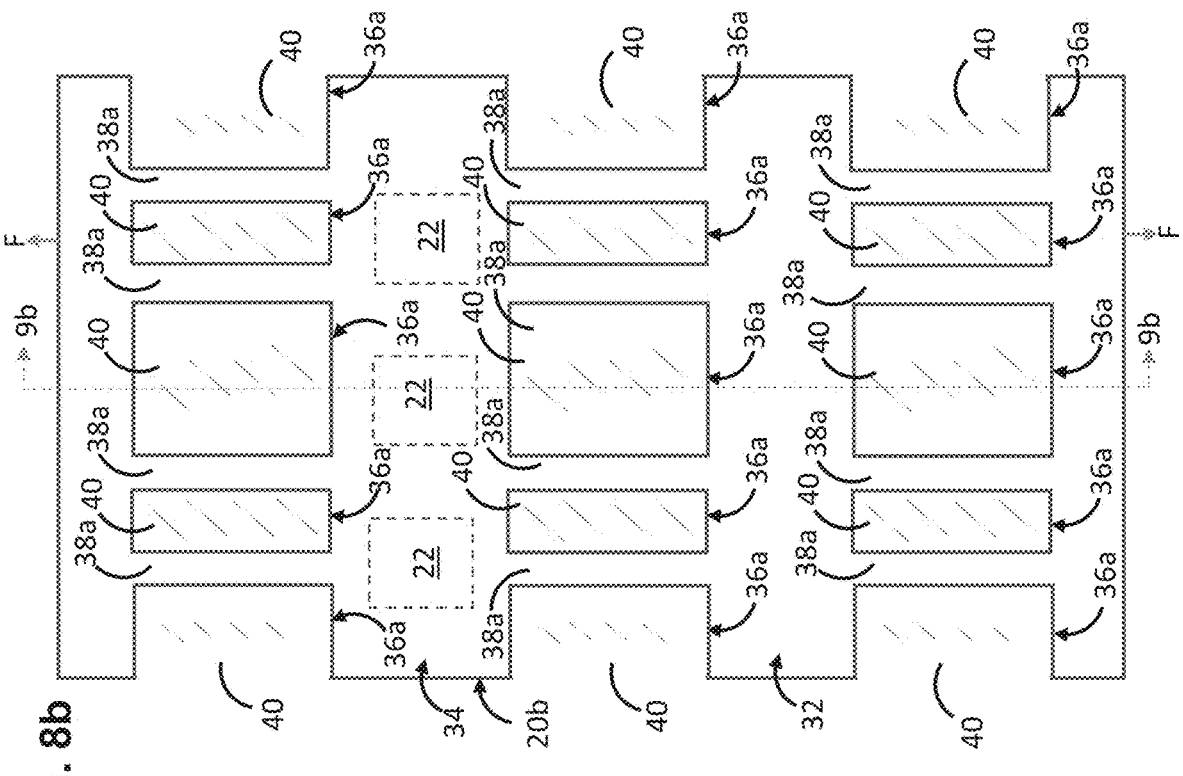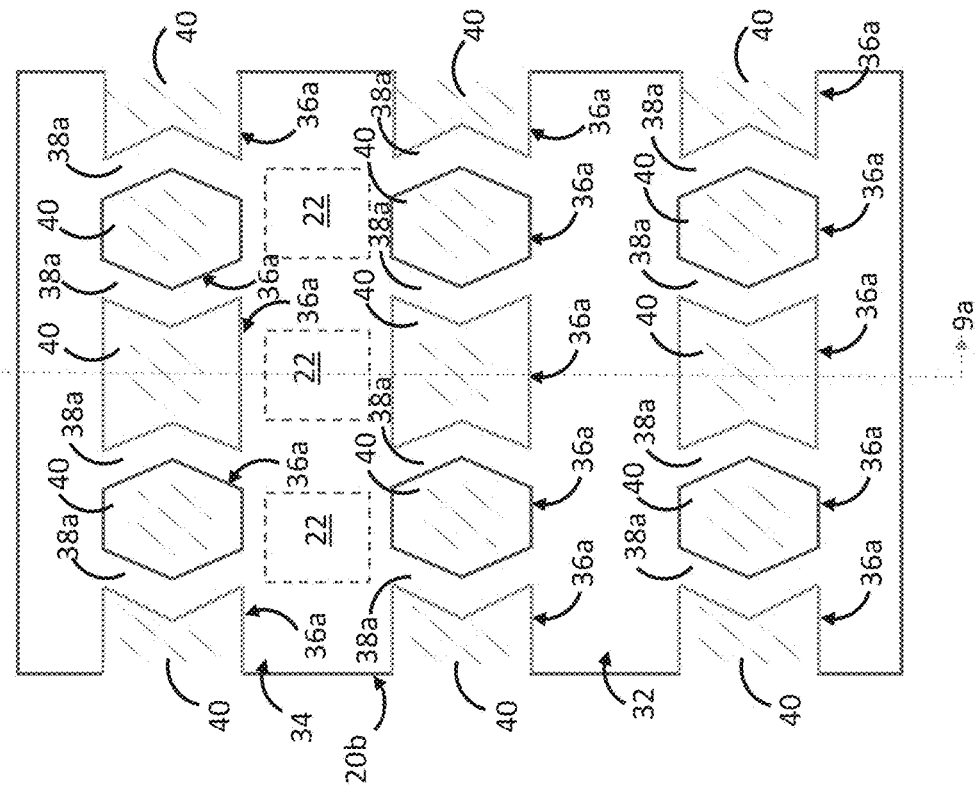

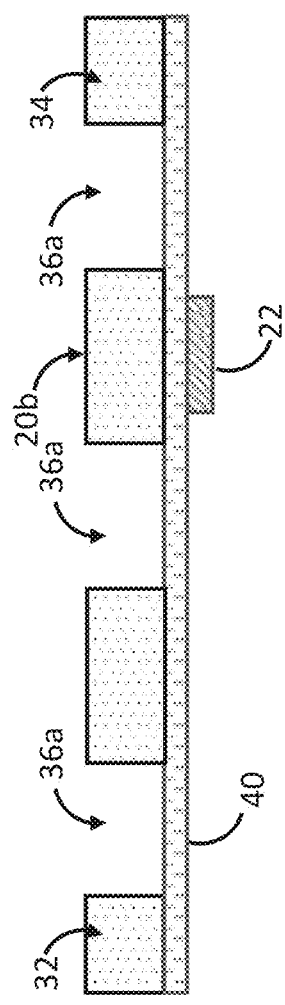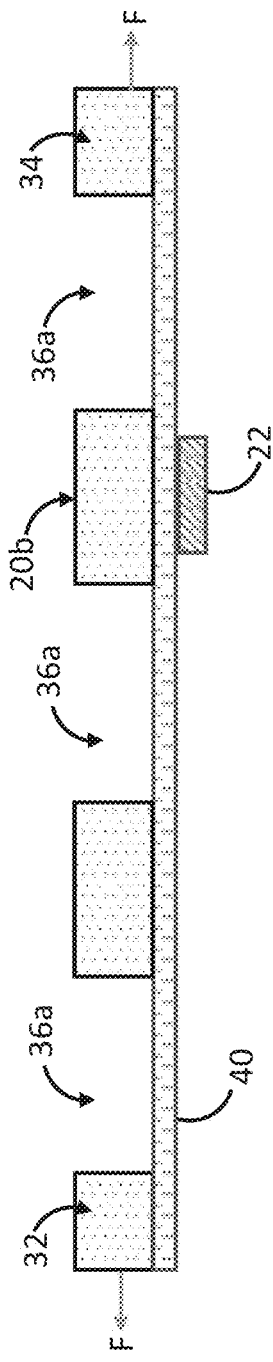

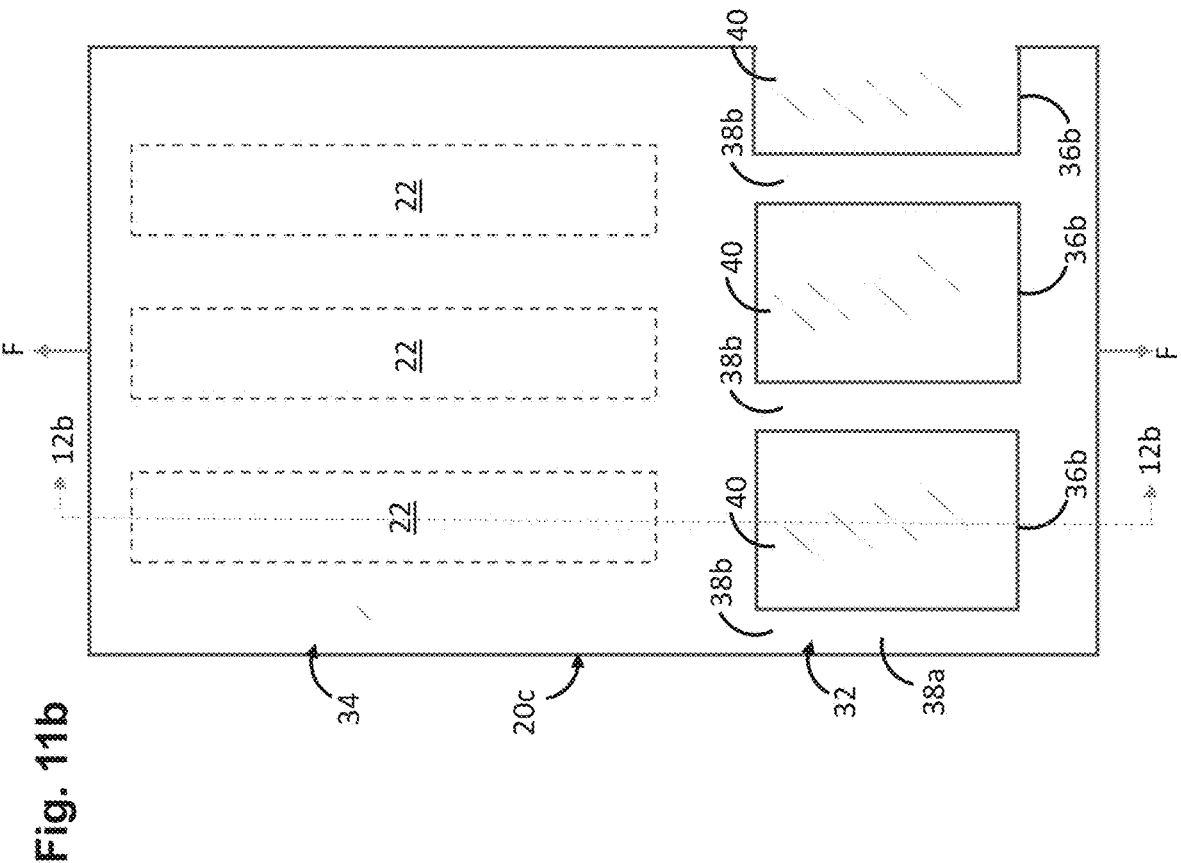
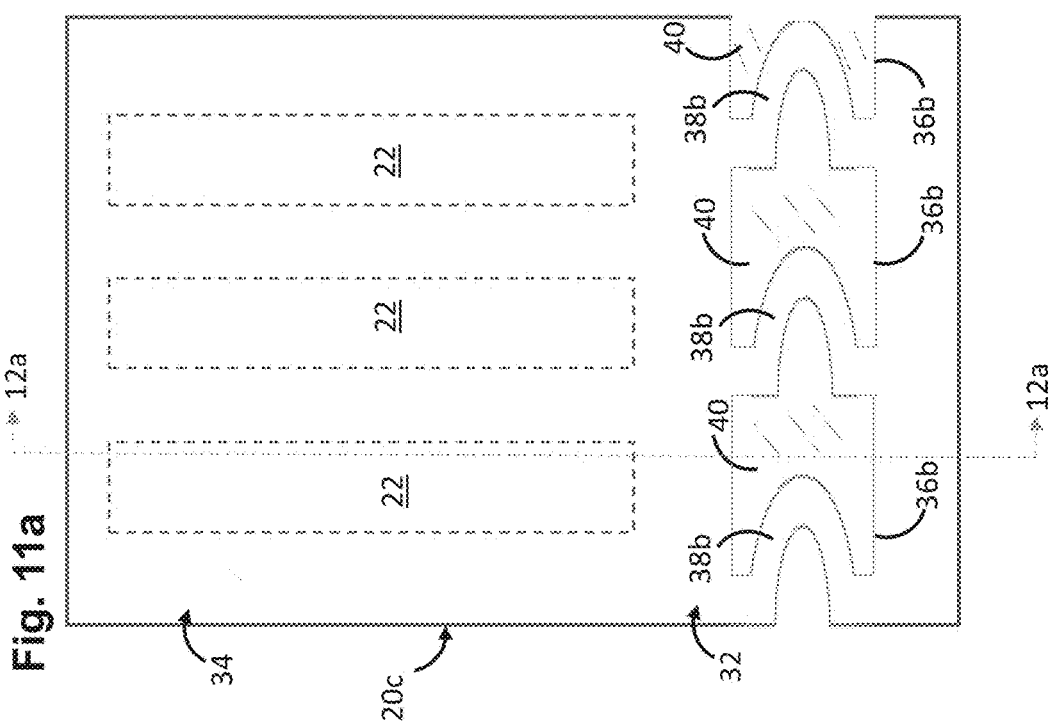

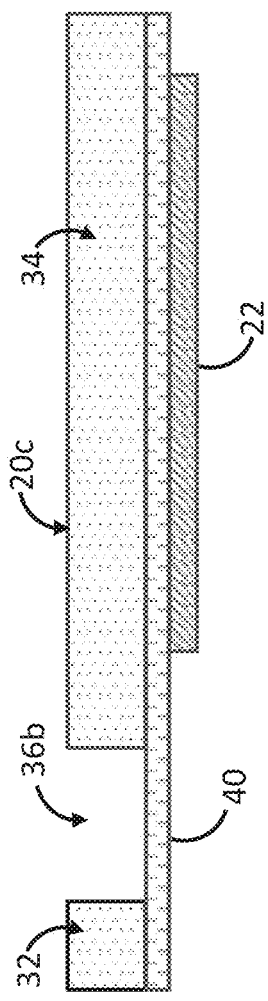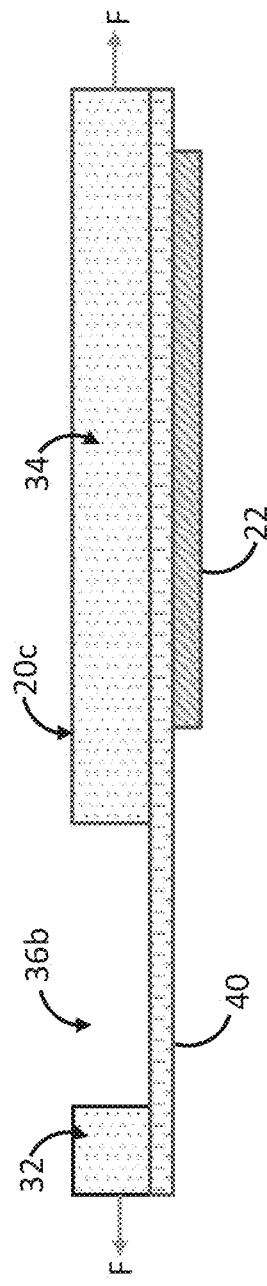

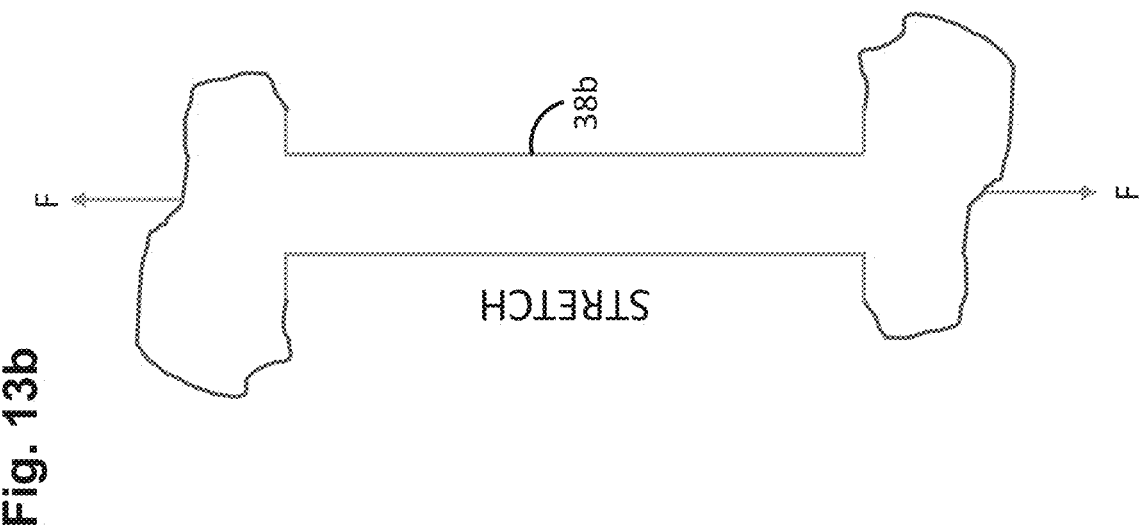
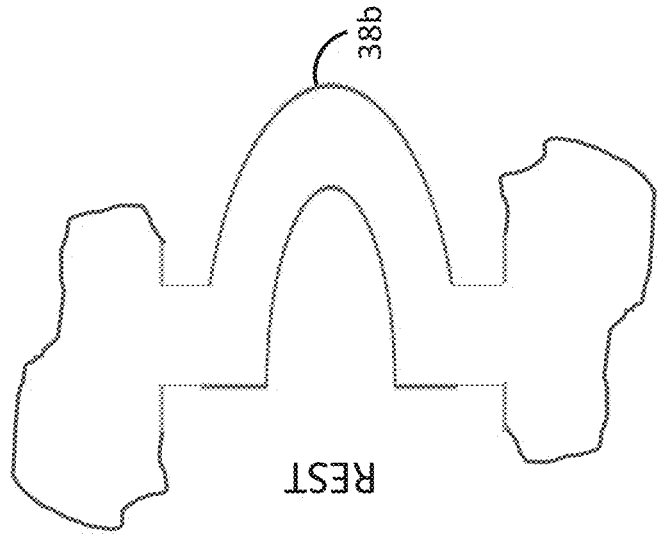

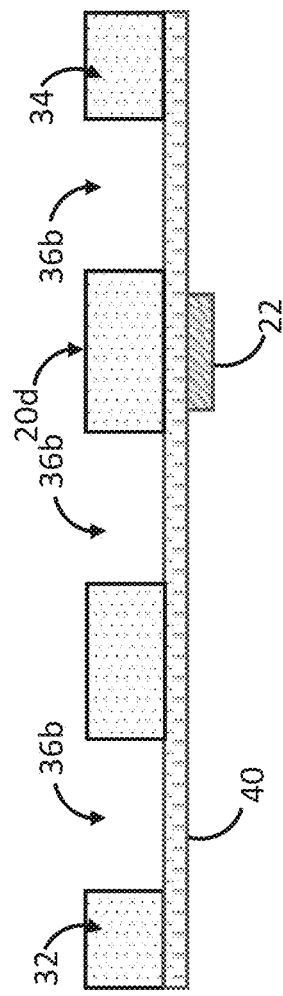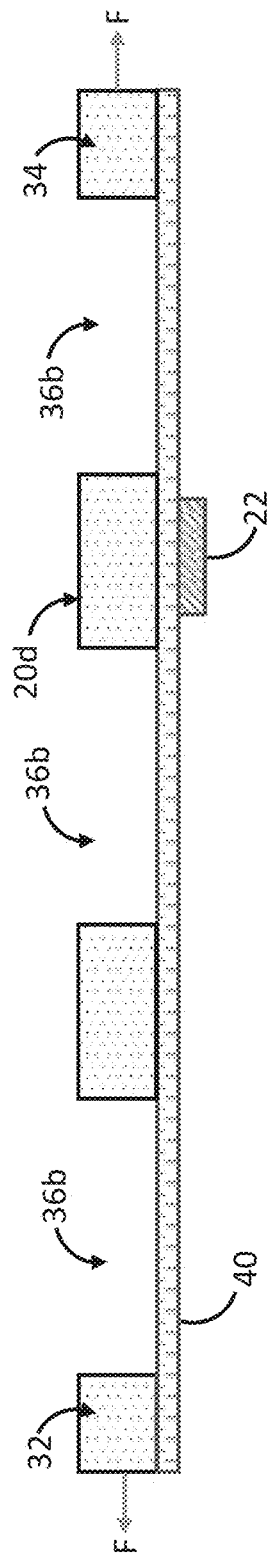

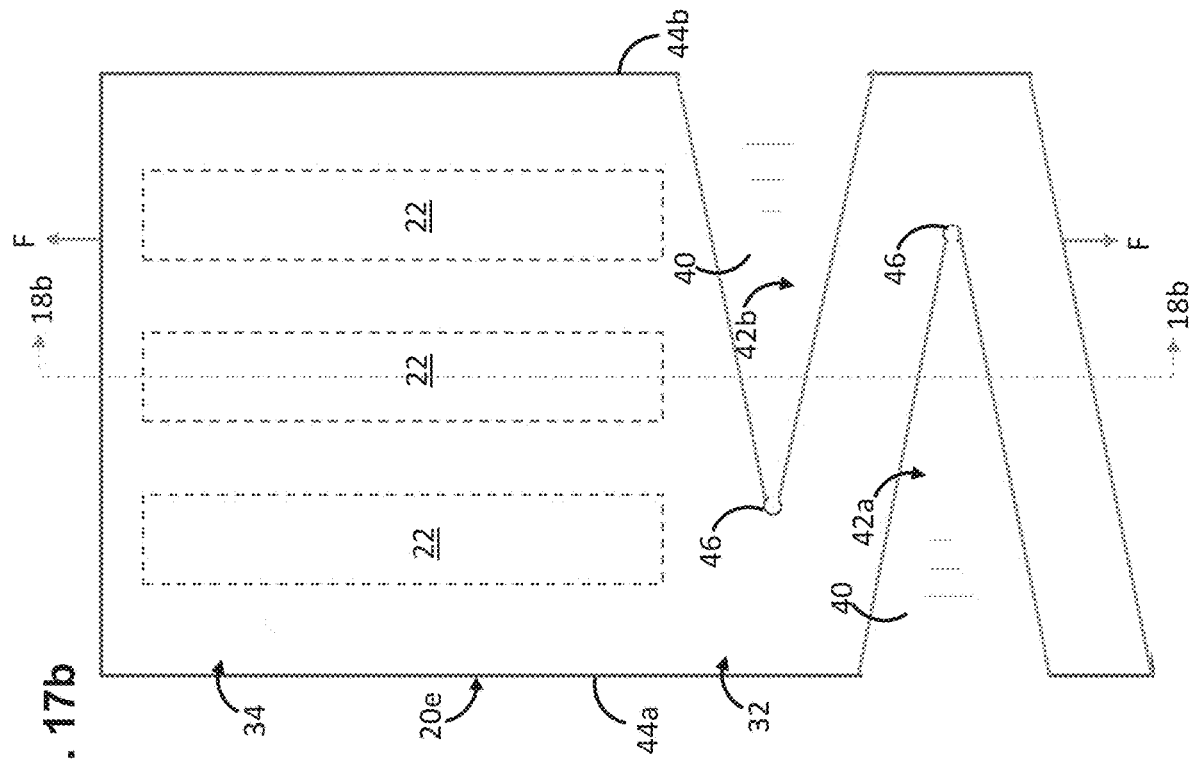
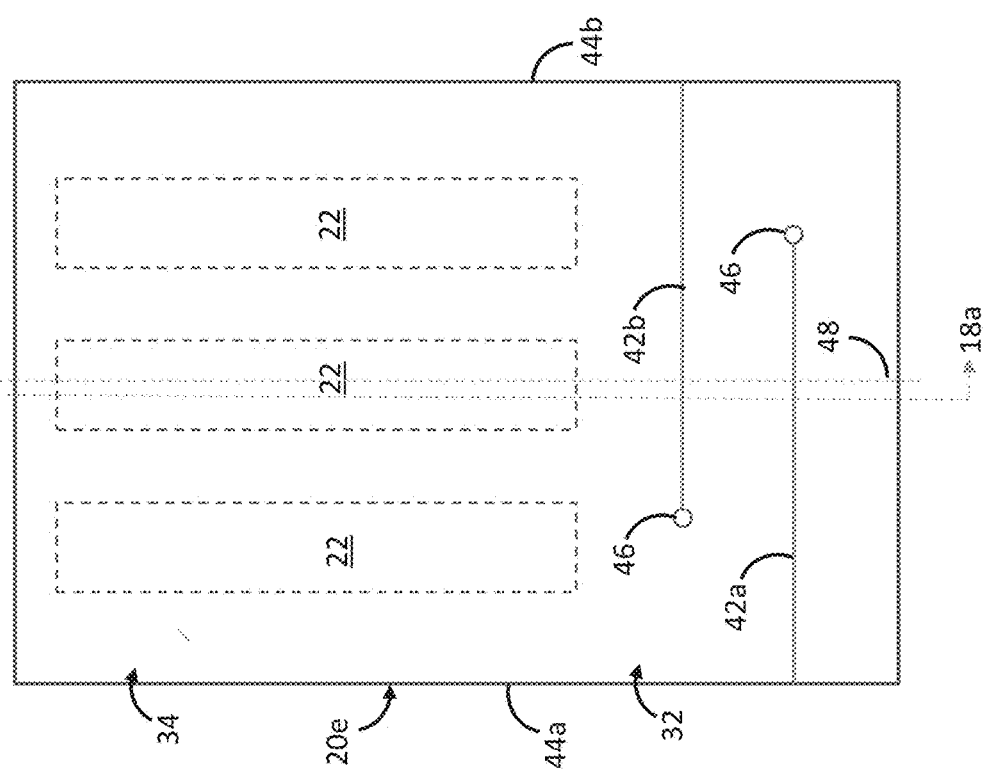

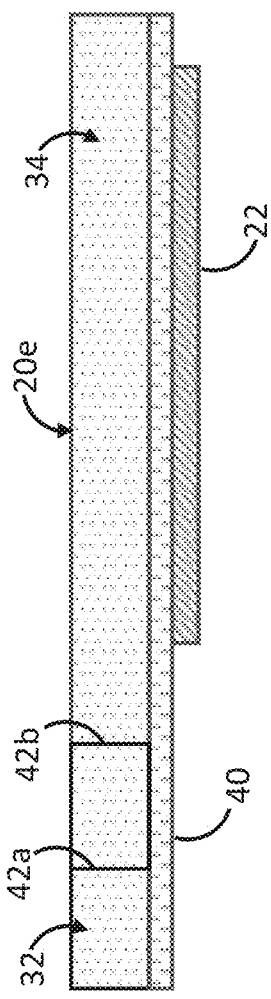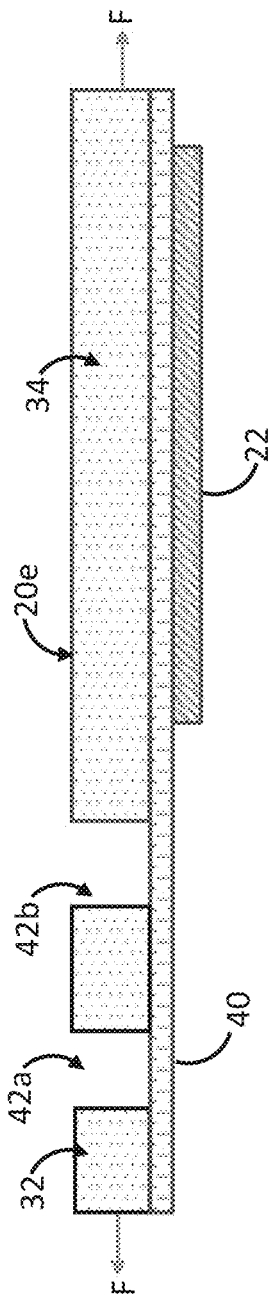

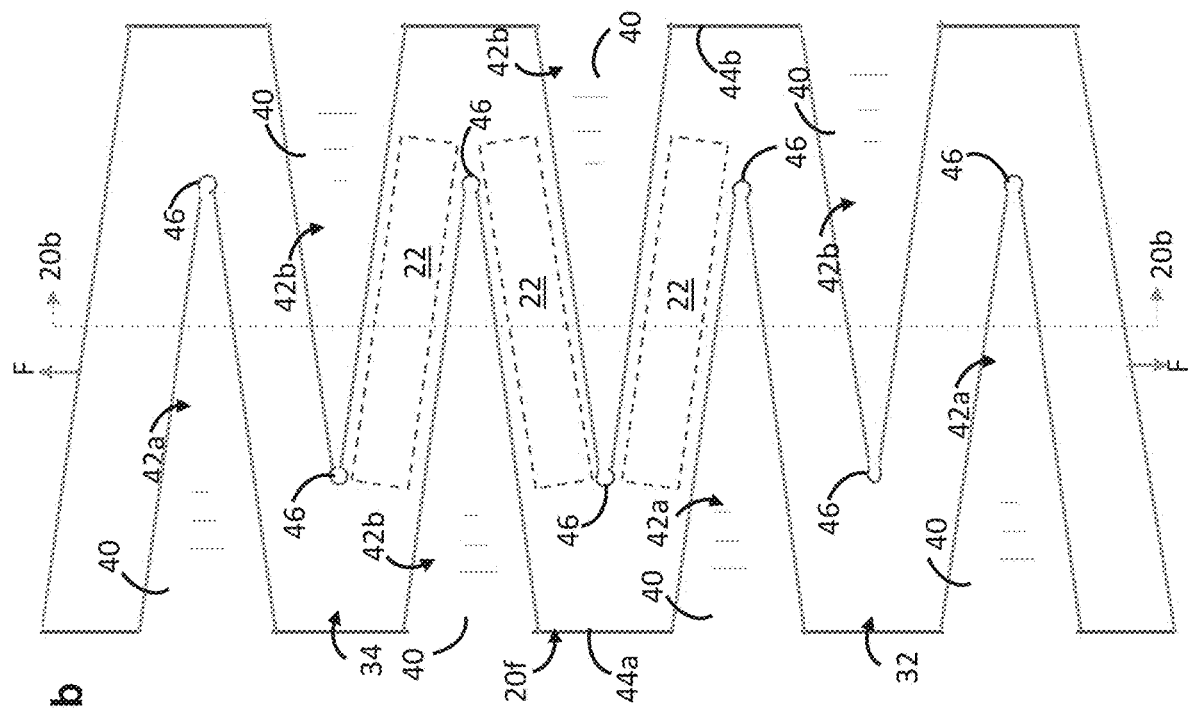
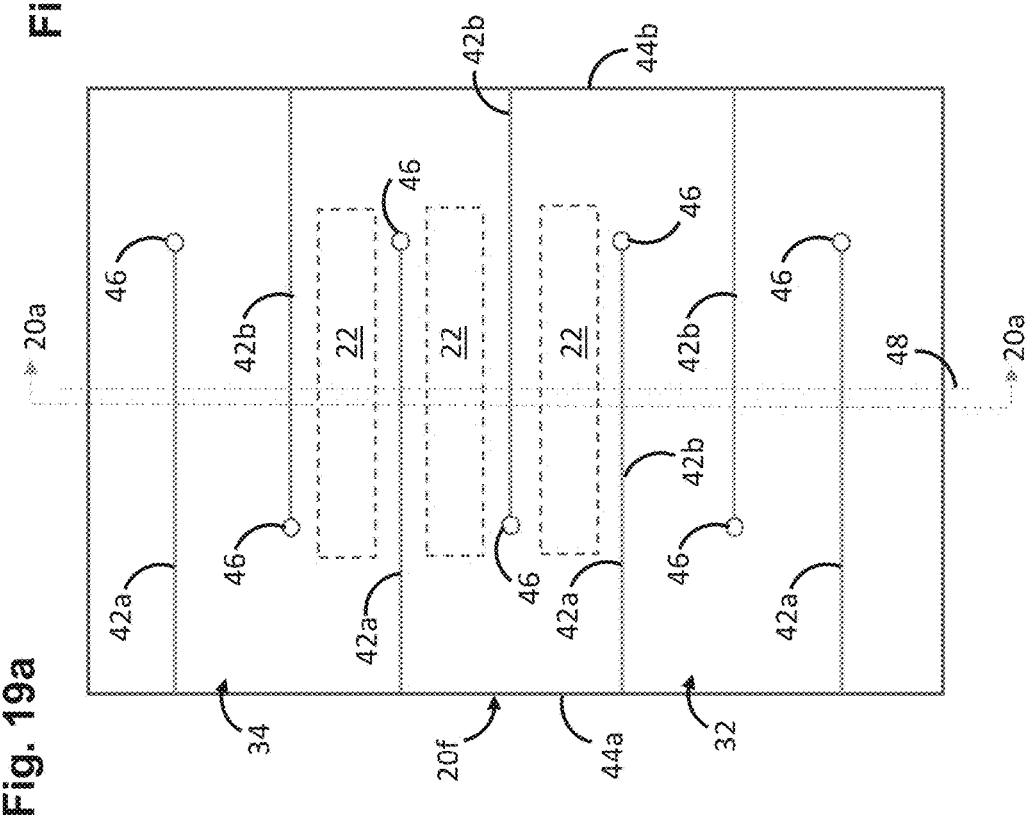

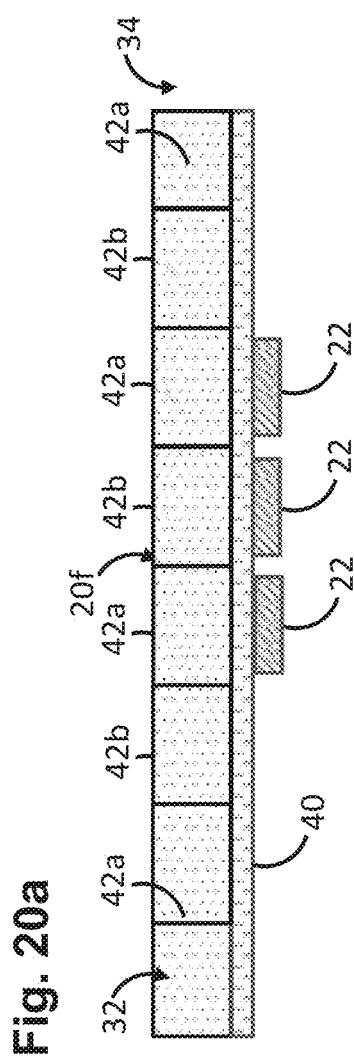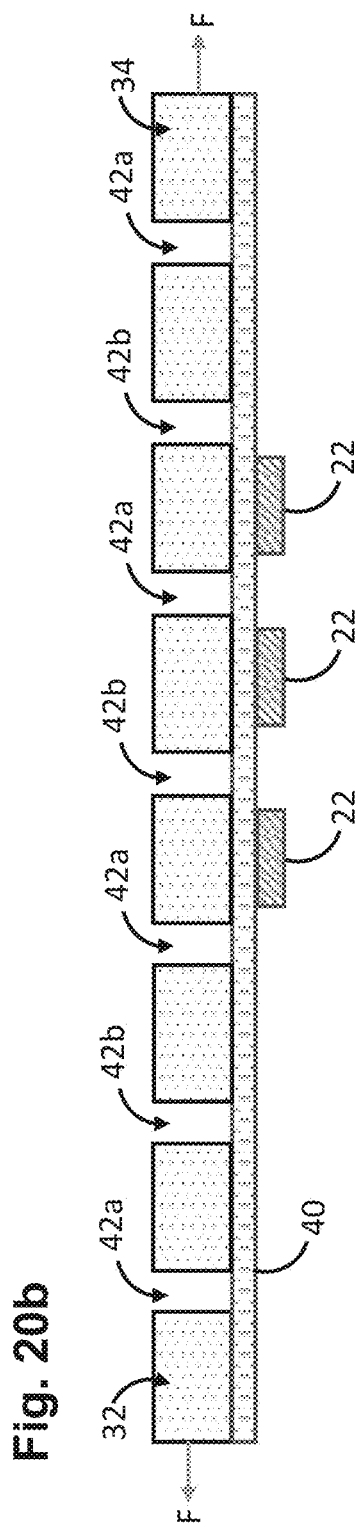

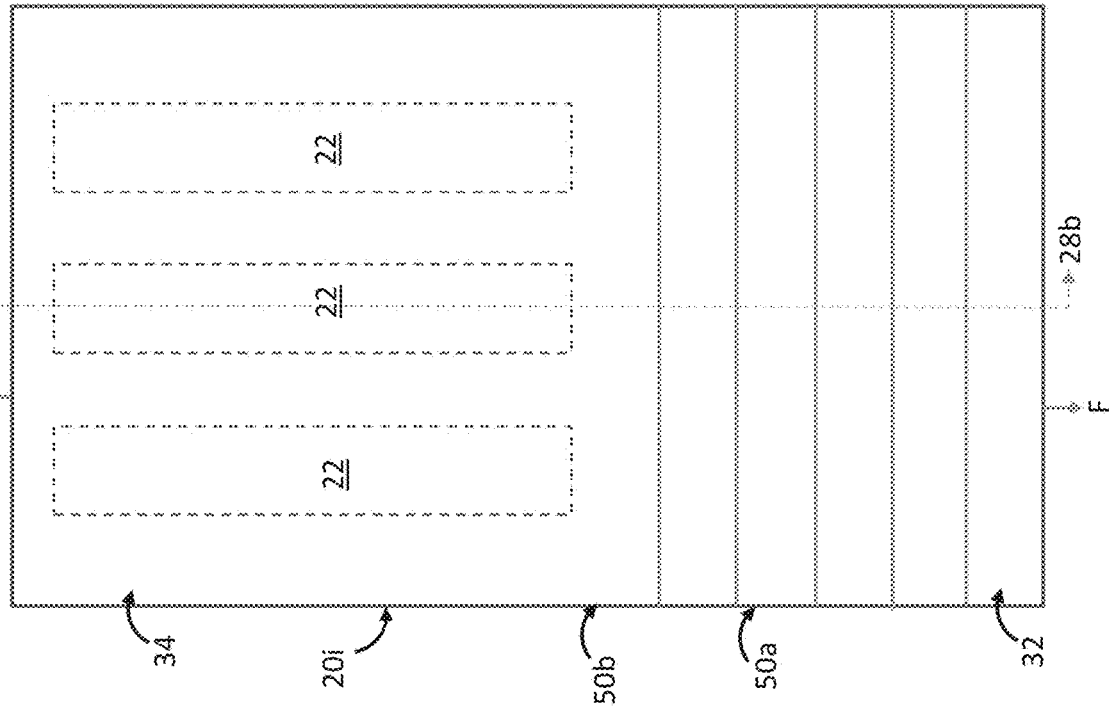
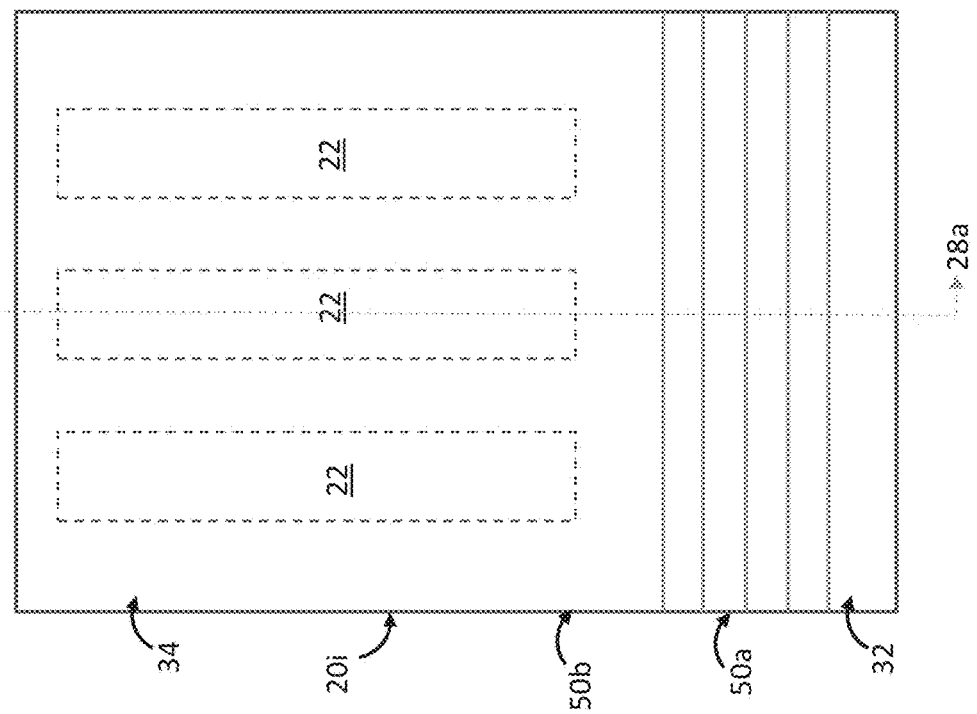

SELF-EXPANDING NERVE CUFF ELECTRODE

RELATED APPLICATION DATA

The present application is a continuation of U.S. patent application Ser. No. 15/967,468, filed Apr. 30, 2018 (now U.S. Pat. No. 10,981,000), which claims the benefit of priority to U.S. Provisional Application Ser. No. 62/500,091, filed on May 2, 2017 and claims the benefit of priority to U.S. Provisional Application Ser. No. 62/500,080, filed on May 2, 2017. The contents of the aforementioned patent applications are hereby expressly incorporated by reference in their entirety.

FIELD OF THE INVENTION

The present invention generally relates to implantable neurostimulation leads, and specifically relates to implantable nerve cuff electrodes that can be used to stimulate nerves to treat ailments, such as obstructive sleep apnea (OSA).

BACKGROUND OF THE INVENTION

Obstructive sleep apnea (OSA) is a common disorder in which the upper airway of a patient can become obstructed (apnea) or partially obstructed (hypopnea) during sleep. It is highly prevalent, affecting 5%-10% of the adult population in the United States, and has serious effects and comorbidities, such as daytime sleepiness, snoring, poor sleep quality, and an increased risk of cardiovascular disease and motor vehicle accidents. Conventional treatments of OSA include using continuous positive airway pressure (CPAP) techniques or performing upper airway surgery. However, due to discomfort, CPAP has a low adherence rate over time, thereby limiting its effectiveness. Alternatively, upper airway surgery is painful and requires a prolonged recovery period, and therefore is used as a last resort to the treatment of OSA, reserved for only extreme cases.

In response to disadvantages of the conventional techniques for treating OSA, a new approach involves stimulating the hypoglossal nerve, which innervates the upper airway muscle, to increase the patency of the upper airway of the patient, thereby preventing or minimizing the onset of OSA. For example, one such neurostimulation system for treating OSA includes a neurostimulator device that stimulates one or more branches of the hypoglossal nerve via electrodes that are implanted at the hypoglossal nerve.

It is desirable that any electrode implanted in contact with a nerve, such as the hypoglossal nerve, continually remain in firm contact with such nerve to maximize the effectiveness of the stimulation regimen. However, certain regions of the patient, such as the neck region, are subject to various dynamic forces that may dislodge or otherwise cause an electrode to migrate from or otherwise temporarily move from its original or desired implantation site, which may have deleterious effect on the stimulation regimen, and thus, the treatment of the ailment, such as OSA.

A reliable solution to this migration problem is to use a nerve cuff electrode device, which can be circumferentially placed around the nerve to deliver effective electrical stimulation to that nerve. This approach provides a more effective anchoring means that keeps the electrode in firm contact with the nerve to which it is attached even when the implantation site is subject to dynamic forces. However, due to the surgical process used to install the nerve cuff electrode around the nerve, the trauma experienced by the nerve will result in nerve swelling, which may expand the circumference of the nerve by as much as 150%.

A conventional approach to securing a nerve cuff electrode to a nerve involves placing the cuff, which is generally C-shaped nerve cuff, around the nerve and securing the cuff using a locking mechanism, such as sutures or other locking means, thereby preventing the nerve cuff from being dislodged. However, the tightly secured cuff electrode may constrict the blood flow to the nerve, essentially strangling it, resulting in damage and even death to the nerve. Although the diameter of the cuff electrode may be sized to accommodate the swelling of the nerve, once the nerve swelling subsides, the cuff electrode needs to reduce its lumen size to form fit around the nerve. The major problem with conventional cuff electrodes is that having a fixed lumen size cannot accommodate changes in the diameter of a nerve which can swell and then reduces its diameter post swelling.

There, thus, remains a need for a nerve cuff electrode design that does not cause nerve constriction when the nerve swells and yet, is able to provide effective nerve stimulation when the nerve stops swelling and the nerve diameter decreases to a size that is closer to original size.

SUMMARY OF THE INVENTION

In accordance with the present invention, an electrode lead comprises an elongated lead body having a proximal end and a distal end, at least one lead connector terminal affixed to the proximal end of the lead body, and a biologically compatible, elastic, electrically insulative cuff body affixed to the distal end of the lead body, at least one electrode contact affixed to the cuff body, and at least one electrical conductor extending through the lead body between the lead connector terminal(s) and the electrode contact(s). The cuff body is configured for being circumferentially disposed around a nerve. The cuff body may be, e.g., composed of silicone, and may have a thickness less than 1 mm. The electrode contact(s) may be configured for being on an inner surface of the cuff body when disposed around the nerve. The electrode lead may further comprise a locking feature configured for firmly securing the cuff body around the nerve.

In accordance with a first aspect of the present invention, the cuff body comprises a plurality of cutouts that increase the expandability of the cuff body when disposed around the nerve. The cutouts may for a plurality of struts (e.g., chevron-shaped struts, which may be alternately angled in opposite directions, or U-shaped struts). In one embodiment, the cuff body has opposing first and second regions, and the cutouts are only in the first region of the cuff body, and the electrode contact(s) are affixed to the second region of the cuff body.

In accordance with a second aspect of the present invention, the cuff body has opposing first and second edges, and comprises a plurality of slits divided into a first set of slits that extend from the first edge towards a center of the cuff body, and a second set of slits that extend from the second edge towards the center of the cuff body, thereby increasing the expandability of the cuff body when disposed around a nerve. In one embodiment, the first and second sets of slits alternate with each other, and may extend past a centerline between the first and second edges of the cuff body. In another embodiment, the first and second sets of slits are aligned with each other, but do not extend past a centerline between the first and second edges of the cuff body. In this case, the cuff body may further comprise a third set of slits extending through the centerline, but not extending to the first and second edges of the cuff body. The third set of slits and first and second sets of slits may alternate with each other. The cuff body may optionally comprise a plurality of circular relief cutouts disposed at the ends of the slits opposite the respective first and second edges from which the slits extend. In one embodiment, the cuff body has opposing first and second regions, the slits are only in the first region of the cuff body, and the electrode contact(s) are affixed to the second region of the cuff body.

In accordance with a third aspect of the present invention, the cuff body comprises an unwrinkled portion and a wrinkled portion, thereby increasing the expandability of the cuff body when disposed around a nerve. The unwrinkled portion and the wrinkled portion may have the same thickness. In one embodiment, the cuff body comprises first and second regions opposite to each other, the unwrinkled portion is incorporated into the first region, and the wrinkled portion is incorporated into the second region, such that the wrinkled portion is configured for overlapping the unwrinkled portion when the cuff body is disposed around the nerve. The electrode contact(s) may be affixed to the second region of the cuff body.

In accordance with a fourth aspect of the present invention, the cuff body comprises a thicker portion and a thinner portion, thereby increasing the expandability of the cuff body when disposed around a nerve. In one embodiment, the cuff body comprises first and second regions opposite to each other, wherein the thicker portion is incorporated into the first region, and the thinner portion is incorporated into the second region, such that the thinner portion is configured for overlapping the thicker portion when the cuff body is disposed around the nerve. The electrode contact(s) may be affixed to the second region of the cuff body.

In accordance with a fifth aspect of the present invention, the cuff body comprises first and second opposing regions, and a serpentine strap extending from the first region cuff body. The strap is configured for being affixed to the second region of the cuff body, thereby increasing the expandability of the cuff body when disposed around a nerve.

In accordance with a sixth aspect of the present inventions, the cuff body comprises one or both of cutouts or slits, thereby increasing the expandability of the cuff body when disposed around a nerve, and a thin stretchable film affixed to the cuff body over cutouts and/or slits. The cutouts and/or slits may have arranged in the manner described above. The thin stretchable film may, e.g., be composed of silicone. The cuff body may have a thickness less than 1 mm, and the thin stretchable film may have a thickness less than 0.5 mm, and perhaps less than 0.1 mm.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 2 is a plan view of one embodiment of the cuff electrode of the electrode lead of FIG. 1, which can be rolled up and circumferentially disposed around a nerve;

FIG. 3 is a cross-sectional view of the cuff electrode of FIG. 2, taken along the line 3-3;

FIG. 6a is a cross-sectional view of the cuff electrode of FIG. 5a, taken along the line 6a-6a;

FIG. 6b is a cross-sectional view of the cuff electrode of FIG. 5b, taken along the line 6b-6b;

FIG. 7a is a plan view of a relaxed strut of the cuff electrode of FIG. 4a;

FIG. 8a is a plan view of an alternative embodiment of the cuff electrode of FIG. 4a in an unrolled form and in the absence of a tensile force;

FIG. 8b is a plan view of an alternative embodiment of the cuff electrode of FIG. 4b in an unrolled form and in the presence of a tensile force;

FIG. 9a is a cross-sectional view of the cuff electrode of FIG. 8a, taken along the line 9a-9a;

FIG. 9b is a cross-sectional view of the cuff electrode of FIG. 8b, taken along the line 9b-9b;

FIG. 11a is a plan view of the cuff electrode of FIG. 10a in an unrolled form and in the absence of a tensile force;

FIG. 11b is a plan view of the cuff electrode of FIG. 10b in an unrolled form and in the presence of a tensile force;

FIG. 12a is a cross-sectional view of the cuff electrode of FIG. 11a, taken along the line 12a-12a;

FIG. 12b is a cross-sectional view of the cuff electrode of FIG. 11b, taken along the line 12b-12b;

FIG. 13a is a plan view of a relaxed strut of the cuff electrode of FIG. 10a;

FIG. 13b is a plan view of a stretched strut of the cuff electrode of FIG. 10b;

FIG. 15a is a cross-sectional view of the cuff electrode of FIG. 14a, taken along the line 15a-15a;

FIG. 15b is a cross-sectional view of the cuff electrode of FIG. 14b, taken along the line 15b-15b;

FIG. 17a is a plan view of the relaxed cuff electrode of FIG. 16a in an unrolled form and in the absence of a tensile force;

FIG. 17b is a plan view of the expanded cuff electrode of FIG. 16b in an unrolled form and in the presence of a tensile force;

FIG. 18a is a cross-sectional view of the cuff electrode of FIG. 17a, taken along the line 18a-18a;

FIG. 18b is a cross-sectional view of the cuff electrode of FIG. 17b, taken along the line 18b-18b;

FIG. 19a is a plan view of an alternative embodiment of the relaxed cuff electrode of FIG. 16a in an unrolled form and in the absence of a tensile force;

FIG. 19b is a plan view of the relaxed cuff electrode of FIG. 16b in an unrolled form and in the presence of a tensile force;

FIG. 20a is a cross-sectional view of the cuff electrode of FIG. 19a, taken along the line 20a-20a;

FIG. 20b is a cross-sectional view of the cuff electrode of FIG. 19b, taken along the line 20b-20b;

FIG. 23a is a cross-sectional view of the cuff electrode of FIG. 22a, taken along the line 23a-23a;

FIG. 25a is a cross-sectional view of the cuff electrode of FIG. 24a, taken along the line 25a-25a;

FIG. 27a is a plan view of the relaxed cuff electrode of FIG. 26a in an unrolled form;

FIG. 27b is a plan view of the expanded cuff electrode of FIG. 26b in an unrolled form;

FIG. 28a is a cross-sectional view of the cuff electrode of FIG. 26a, taken along the line 28a-28a;

FIG. 31a is a cross-sectional view of the cuff electrode of FIG. 29a, taken along the line 31a-31a;

FIG. 34a is a cross-sectional view of the cuff electrode of FIG. 32a, taken along the line 34a-34a.

DETAILED DESCRIPTION OF THE EMBODIMENTS

Figure 1:
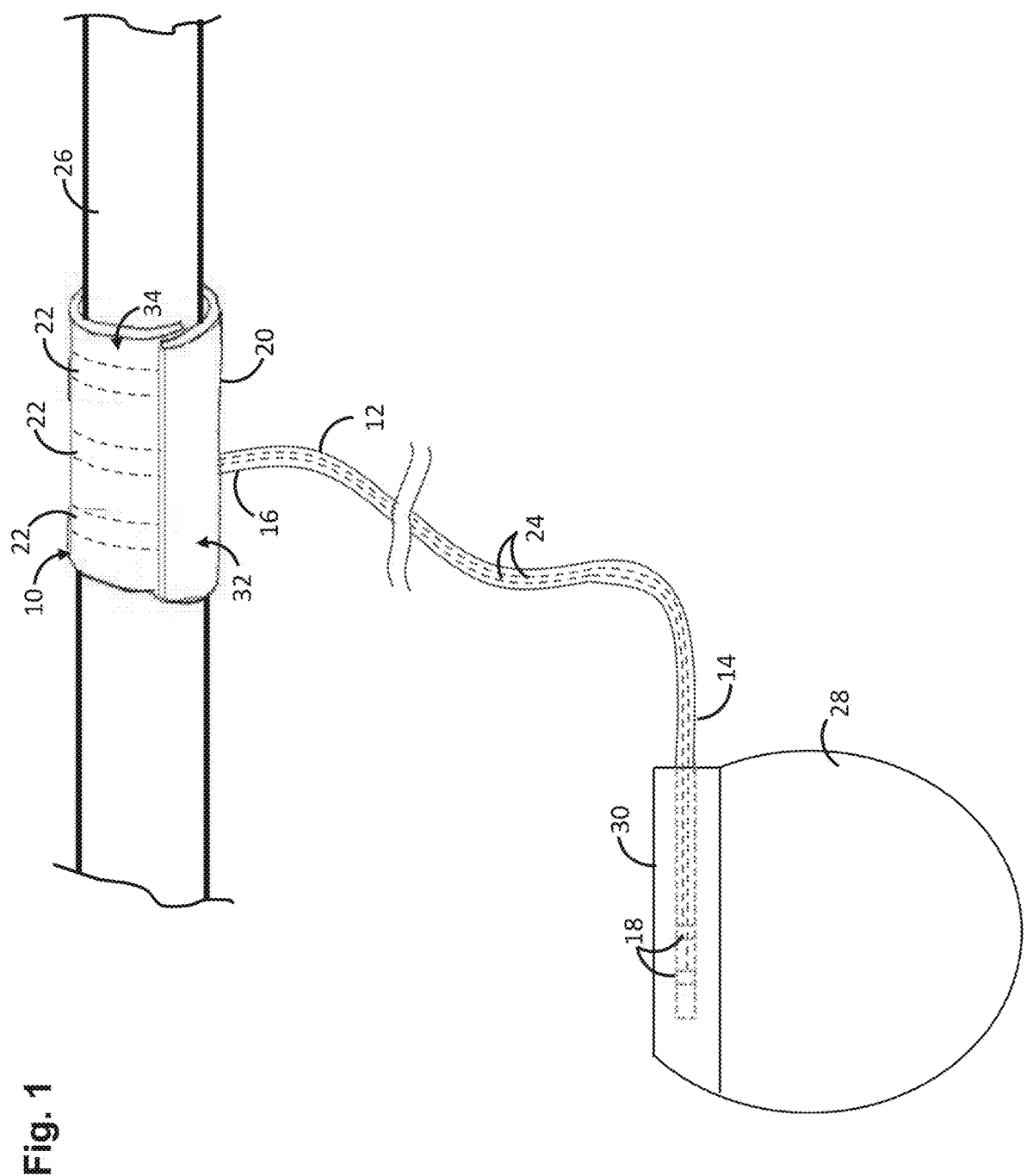
FIG. 1 is a perspective view of an electrode lead with a nerve cuff electrode constructed in accordance with one embodiment of the present inventions.

Referring first to FIGS. 1-3, an electrode lead 10 constructed in accordance with one embodiment will now be described. Although the electrode lead 10 lends itself well to be used in the treatment of OSA by stimulating the hypoglossal nerve, the electrode lead 10 may be used for any medical treatment where it is desired to stimulate a nerve.

The electrode lead 10 generally comprises an elongated lead body 12 having a proximal end 14 and a distal end 16, at least one lead connector terminal 18 (two shown) affixed to the proximal end 14 of the lead body 12, a cuff body 20 affixed to the distal end 16 of the lead body 12, at least one electrode contact 22 (three shown) disposed on the cuff body 20, and at least one electrical conductor 24 (two shown) extending through the lead body between the lead connector terminals 18 and the electrode contacts 22. As shown, the cuff body 20 can be circumferentially disposed around tissue, e.g., a nerve 26, such that the electrode contacts 22 are disposed on an inner surface of the cuff body 20 in contact with the nerve 26.

In the illustrated embodiment, the electrode contacts 22 form a guarded tripolar electrode arrangement (e.g., anode-cathode-anode) that can be used for purposes of stimulating the nerve 26. Two of the electrode contacts 22 (the anodes) are ganged together and coupled to one of the lead connector terminals 18 via an electrical conductor 24, and the remaining electrode contact 22 (the cathode) is coupled to the other lead connector terminal 18 via the other electrical conductor 24. It should be appreciated that, alternatively, the number of electrode contacts 22, lead connector terminals 18, and electrical conductors 24 can be identical, such that electrode contacts 22 may be energized independently of each other.

The lead connector terminals 18 of the proximal end 14 of the lead body 12 can be inserted into a connector block 30 of a neurostimulation device 28, which supplies electrical pulses to the electrode contacts 22 in accordance with a stimulation regimen. Recording electrodes (not shown) can also be connected to the neurostimulation device 28 to provide sensed physiological signals (e.g., electromyogram (EMG) signals) to the neurostimulation device 28. In an alternative embodiment, the electrode contacts 22 of the electrode lead 10 can serve as recording electrodes to detect nerve action potentials.

The lead body 12 and cuff body 20 may be composed of an elastic, electrically insulative, biocompatible, material, such as, e.g., medical-grade silicone, polyurethane, etc. The lead connector terminals 18 may be composed of a suitable electrically conductive material, such as, e.g., stainless steel, and the electrode contacts 22 may be composed of a suitable electrically conductive and biocompatible material, such as gold, or 90/10 or 80/20 Platinum-Iridium alloy. The electrical conductors 24 may likewise be composed of a suitable electrically conductive and biocompatible material, such as MP35N, MP35N with silver core, stainless steel, or tantalum. The cuff body 20 may be relatively thin, e.g., having a thickness less than 1 mm, and in some cases less than 0.5 mm, so that the cuff body 20 may be easily disposed around in conformance with the nerve 26. The cuff body 20 may take the form of a planar sheet, when unrolled (as best shown in FIG. 2), but in its natural state, rolls up on itself to be circumferentially disposed around the nerve 26 (as best shown in FIG. 1). The cuff body 20 has an opposing first region 32 and a second region 34, which when the cuff body 20 is rolled up on itself, may overlap each other. In one embodiment, the cuff body 20 may comprise a strap and buckle arrangement, along with a locking mechanism, that secures the cuff body 20 around the nerve 26, as described in U.S. Provisional Patent Application Ser. No. 62/500,080, entitled "Nerve Cuff Electrode Locking Mechanism," which is expressly incorporated herein by reference.

More significant to the present inventions, and notwithstanding that the cuff body 20 may include features that secure it around the nerve 26, the cuff body 20 can include features that increases the expandability of the cuff body 20 when circumferentially disposed around the nerve 26, thereby better accommodating any swelling of the nerve 26, while allowing the cuff body 20 to retract back to its original size when the swelling of the nerve 26 subsides.

To this end, and with reference to FIGS. 4-7, one embodiment of a cuff body 20a comprises a plurality of cutouts 36a that form a plurality of struts 38a within the first region 32 of the cuff body 20a. In the illustrated embodiment, the struts 38a are chevron-shaped struts that are alternately angled in opposite directions. Alternatively, the chevron-shaped struts 38a are all angled in the same direction. In the absence of the application of a tensile force F on the cuff body 20a, each strut 38a will be relaxed, as illustrated in FIGS. 5a-7a, whereas each strut 38a will stretch and tends towards straightening out in response to the application of a tensile force F along the wall of the cuff body 20a, as illustrated in FIGS. 5b-7b. FIGS. 5a and 5b show for illustrative purposes, the cuff body 20a in an unrolled position, and the relaxed and expanded states of the cuff wall with tension applied to the cuff wall and no tension. In actual use, the wall of the cuff body 20a would be rolled up around a nerve and the radial outward force on the cuff body 20a provided by a swollen nerve would be translated to cuff wall tension. Thus, if the cuff body 20a is properly sized to the nerve 26, each strut 38a will be relaxed (as shown in FIG. 4a) when the nerve 26 around which the cuff body 20a is circumferentially disposed is not swollen, and each strut 38a will stretch and tend to straighten out (as shown in FIG. 4b) when the nerve 26 around which the cuff body 20a is circumferentially disposed is swollen.

Figure 4A:
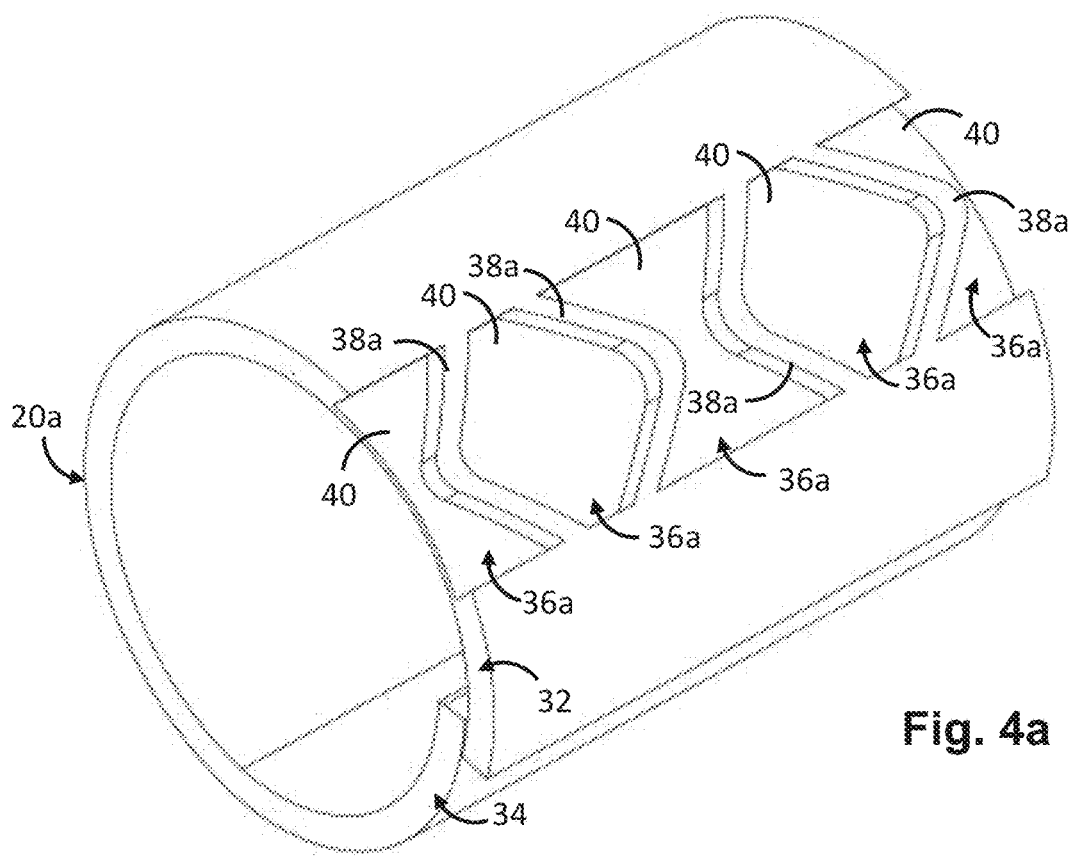
FIG. 4a is a perspective view of one embodiment of the cuff electrode of the electrode lead of FIG. 1, particularly shown in a rolled up, relaxed state.
Figure 4B:
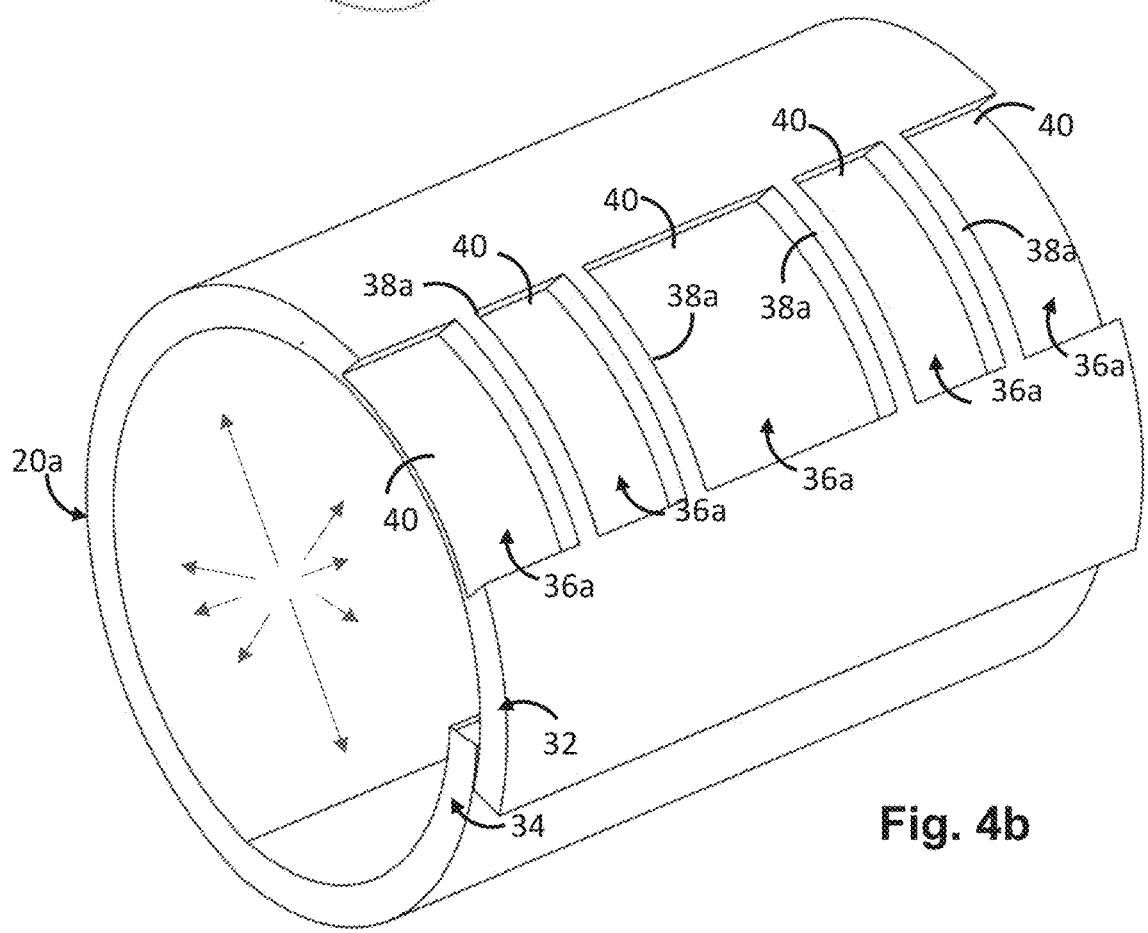
FIG. 4b is a perspective view of the cuff electrode of FIG. 4a, particularly shown in a rolled up, expanded state.
Figure 5A:
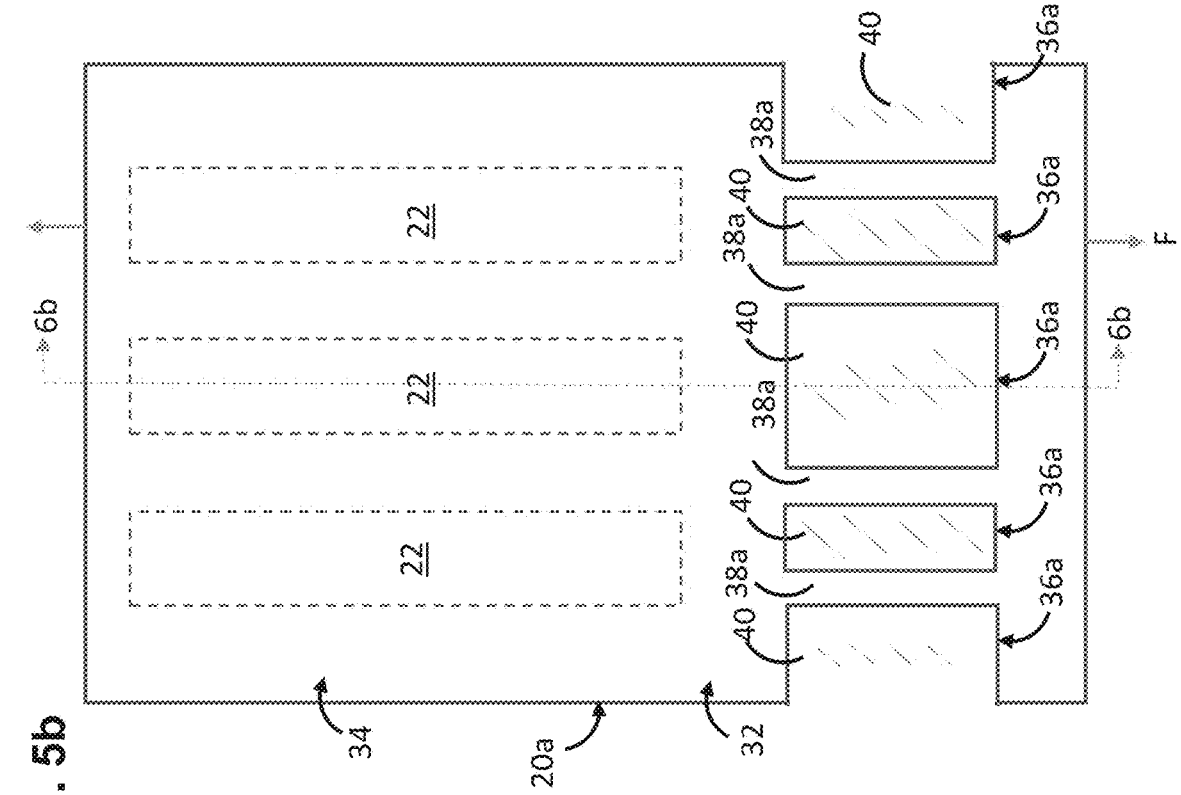
FIG. 5a is a plan view of the cuff electrode of FIG. 4a in an unrolled form and in the absence of a tensile force.
Figure 5B:
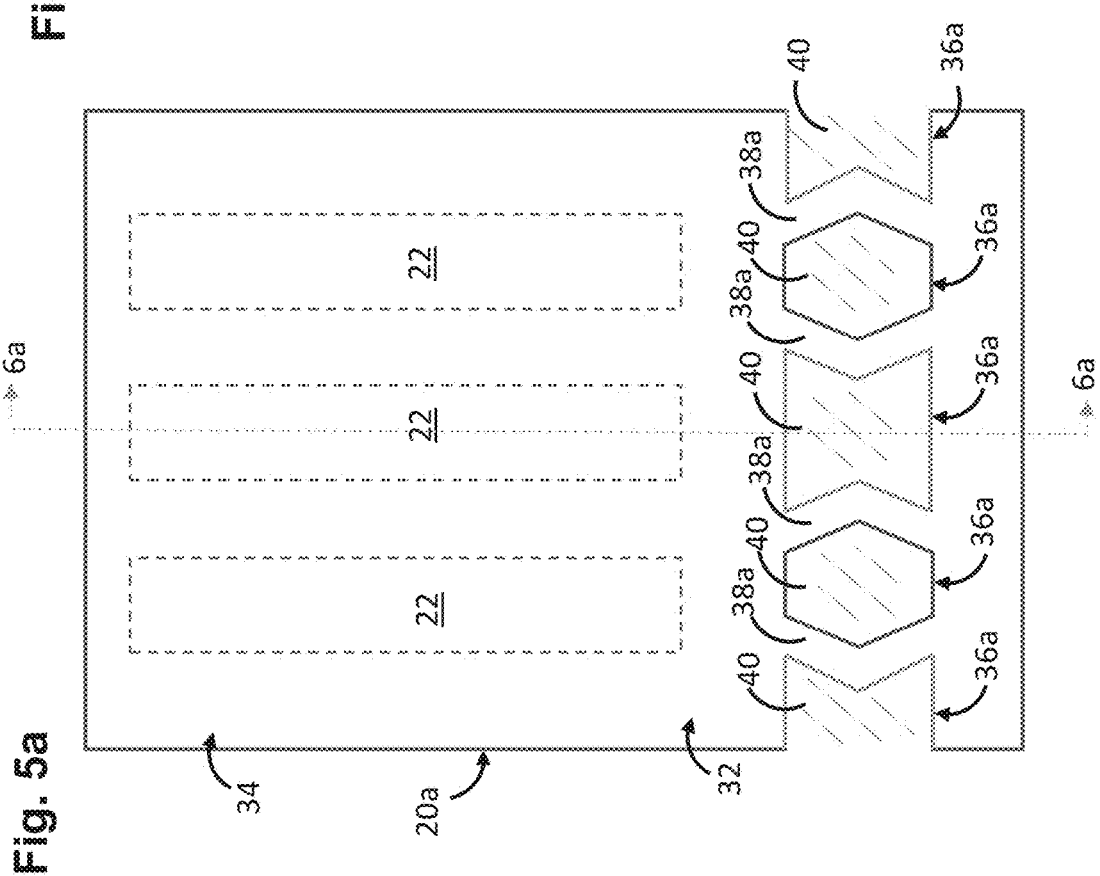
FIG. 5b is a plan view of the cuff electrode of FIG. 4b in an unrolled form and in the presence of a tensile force.
Figure 7A:
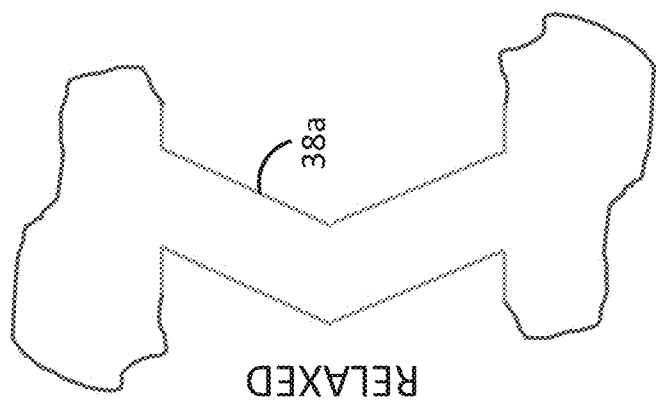
Figure 7B:
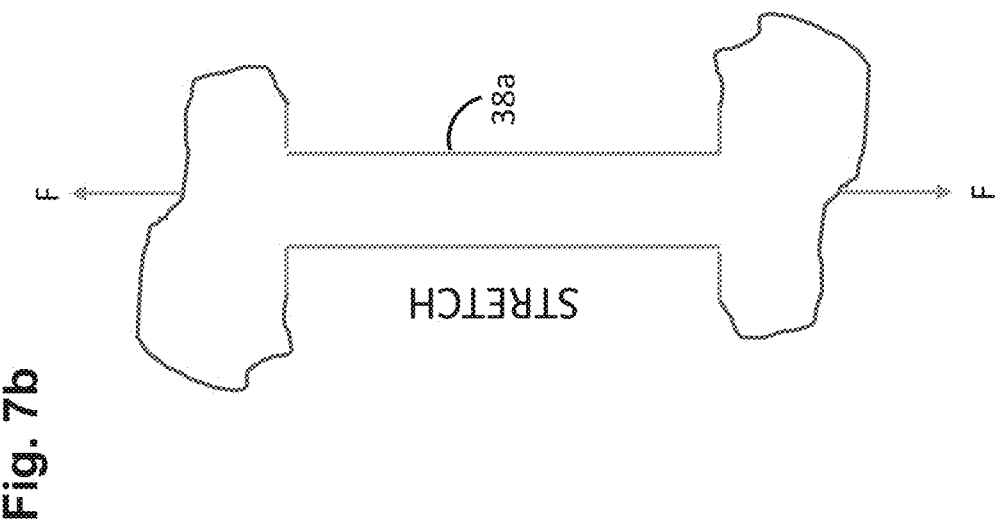
FIG. 7b is a plan view of a stretched strut of the cuff electrode of FIG. 4b.

That is, due to its elastomeric characteristics, when the nerve 26 is not swollen, each strut 38a (FIGS. 5a-7a) will be in a relaxed state of the cuff body 20a (FIG. 4a). In response to the outward radial force applied to the cuff body 20a by the swelling of the nerve 26, thereby generating a tensile force F, each strut 38a may stretch (FIGS. 5b-7b), facilitating the transition of the cuff body 20a from its relaxed state (FIG. 4a) to its stretched, expanded state (FIG. 4b). In response to the decrease in the outward radial force applied to the cuff body 20a as the swelling of the nerve 26 subsides, thereby diminishing or completely removing the tensile force F, each strut 38a may again relax (FIGS. 5a-7a), facilitating the transition of the cuff body 20a from its expanded state (FIG. 4b) back to its relaxed state (FIG. 4a). Thus, it can be appreciated that the increase in the flexibility of the cuff body 20a by the inclusion of the cutouts 36a and use of struts 38a prevents, or at least minimizes, the strangling of the nerve 26 as it swells, thereby allowing sufficient flow of blood and other nutrients to the nerve 26.

In an optional embodiment, the cuff body 20 may further comprise a thin stretchable film 40 affixed (e.g., via bonding) to the cuff body 20a underneath and completely covering the cutouts 36a. The thin stretchable film 40 may be on the inner surface of the cuff body 20a when the cuff body 20a is rolled up on itself. Although the thin stretchable film 40 may help limit the expansion of the cuff body 20a in response to the swelling of the nerve 26, the thin stretchable film 40 may also help to facilitate restoration of the cuff body 20a back to its original relaxed state. Furthermore, the thin stretchable film 40 prevents connective tissue from growing into or out of the cutouts 36a in the cuff body 20a. In addition, the film 40 blocking the openings of the cutouts 36a prevents undesired shunting of electrical current through the cutouts 36a, which would cause an inefficiency in stimulation.

Although the cutouts 36a and corresponding struts 38a are illustrated in FIGS. 4a, 4b, 5a, and 5b as being formed only in the first region 32 of the cuff body 20a, it should be appreciated that the cutouts 36a and corresponding struts 38a may be formed in the entirety of a cuff body 20b illustrated in FIGS. 8 and 9. As in the case with the cuff body 20a illustrated in FIGS. 4-7, in the absence of the application of a tensile force F on the cuff body 20b, each strut 38a will be relaxed, as illustrated in FIGS. 8a and 9a, whereas each strut 38a will stretch and tends towards straightening out in response to the application of a tensile force F on the cuff body 20b, as illustrated in FIGS. 8b and 9b. However, because there are three rows of cutouts 36a and corresponding struts 38a in the cuff body 20b, the expandability of the cuff body 20b is further increased relative to the expandability of the cuff body 20a. As with the embodiment illustrated in FIGS. 4-7, a thin stretchable film 40 may be affixed (e.g., via bonding) to the cuff body 20b underneath and completely covering the cutouts 36a to provide the aforementioned advantages.

In an alternative embodiment illustrated in FIGS. 10-13, a cuff body 20c comprises a plurality of cutouts 36b that create a plurality of U-shaped struts 38b. Similar to the cuff body 20a illustrated in FIGS. 4-7, in the absence of the application of a tensile force F on the cuff body 20c, each strut 38b will be relaxed, as illustrated in FIGS. 11a-13a, whereas each strut 38b will stretch and tends towards straightening out in response to the application of a tensile force F on the cuff body 20c, as illustrated in FIGS. 11b-13b. Thus, if the cuff body 20c is properly sized to the nerve 26, each strut 38b will be relaxed (as shown in FIG. 10a) when the nerve 26 around which the cuff body 20c is circumferentially disposed is not swollen, and will stretch (as shown in FIG. 10b) when the nerve 26 around which the cuff body 20c is circumferentially disposed is swollen.

Figure 10A:
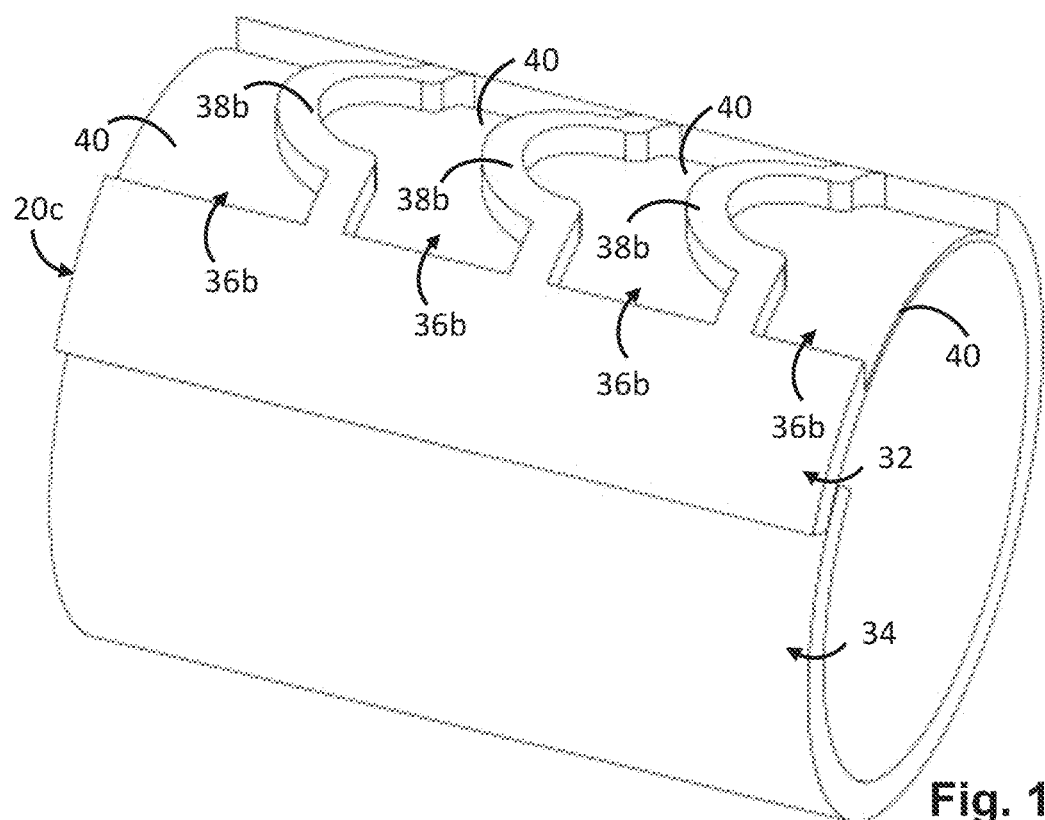
FIG. 10a is a perspective view of another embodiment of the cuff electrode of the electrode lead of FIG. 1, particularly shown in a rolled up, relaxed state.
Figure 10B:
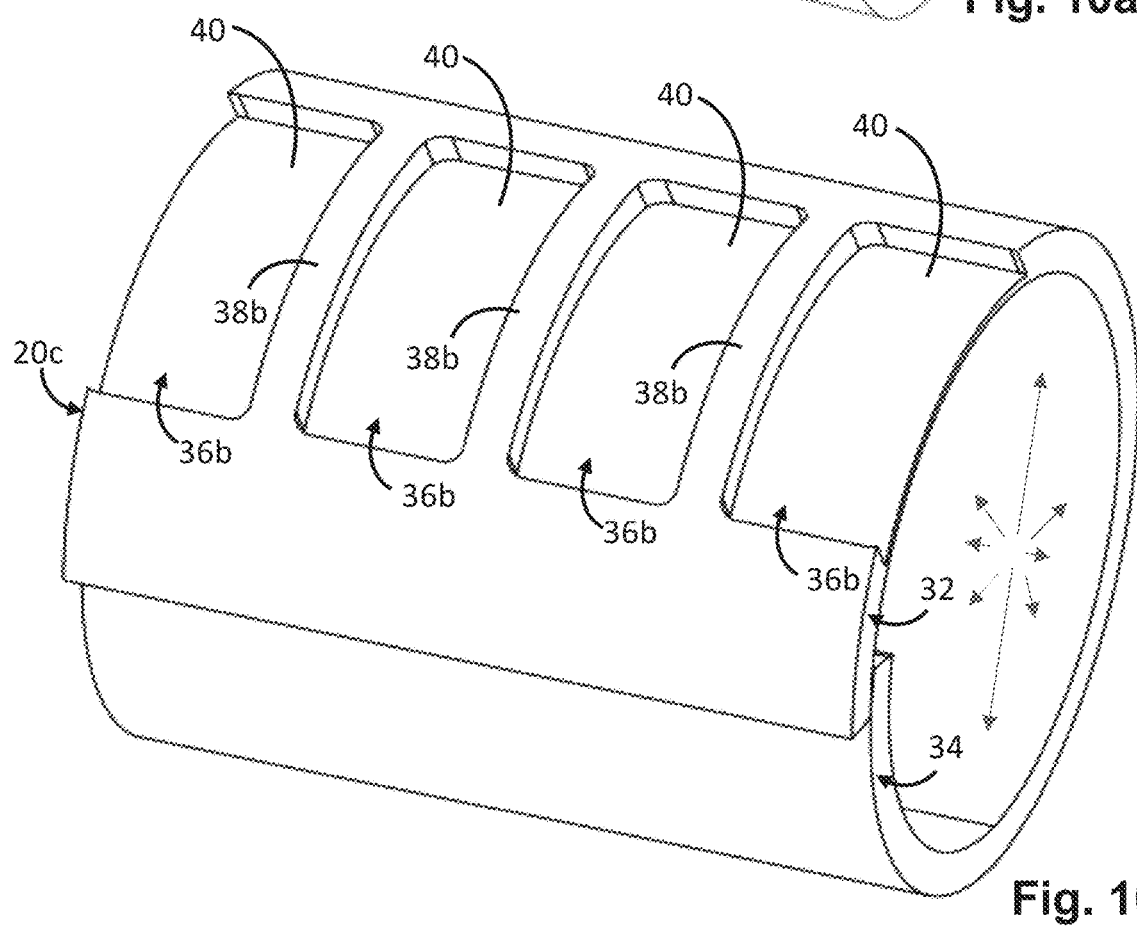
FIG. 10b is a perspective view of the cuff electrode of FIG. 10a, particularly shown in a rolled up, expanded state.

That is, due to its elastomeric characteristics, when the nerve 26 is not swollen, each strut 38b may be at rest (FIGS. 11a-13a) corresponding to the relaxed state of the cuff body 20c (FIG. 10a). In response to the outward radial force applied to the cuff body 20c by the swelling of the nerve 26, thereby generating a tensile force F, each strut 38b may stretch (FIGS. 11b-13b), facilitating the transition of the cuff body 20c from its relaxed state (FIG. 10a) to its expanded state (FIG. 10b). In response to the decrease in the outward radial force applied to the cuff body 20c as the swelling of the nerve 26 subsides, thereby diminishing or completely removing the tensile force F, each strut 38b may again relax (FIGS. 11a-13a), facilitating the transition of the cuff body 20c from its expanded state (FIG. 10b) back to its relaxed state (FIG. 10a). Thus, it can be appreciated that the expandability of the cuff body 20c by the inclusion of the cutouts 36b prevents, or at least minimizes, the strangling of the nerve 26 as it swells, thereby allowing sufficient flow of blood and other nutrients to the nerve 26. As with the cuff body 20a illustrated in FIGS. 4-7, a thin stretchable film 40 may be affixed (e.g., via bonding) to the cuff body 20a underneath and completely covering the cutouts 36c to provide the aforementioned advantages.

Figure 14B:
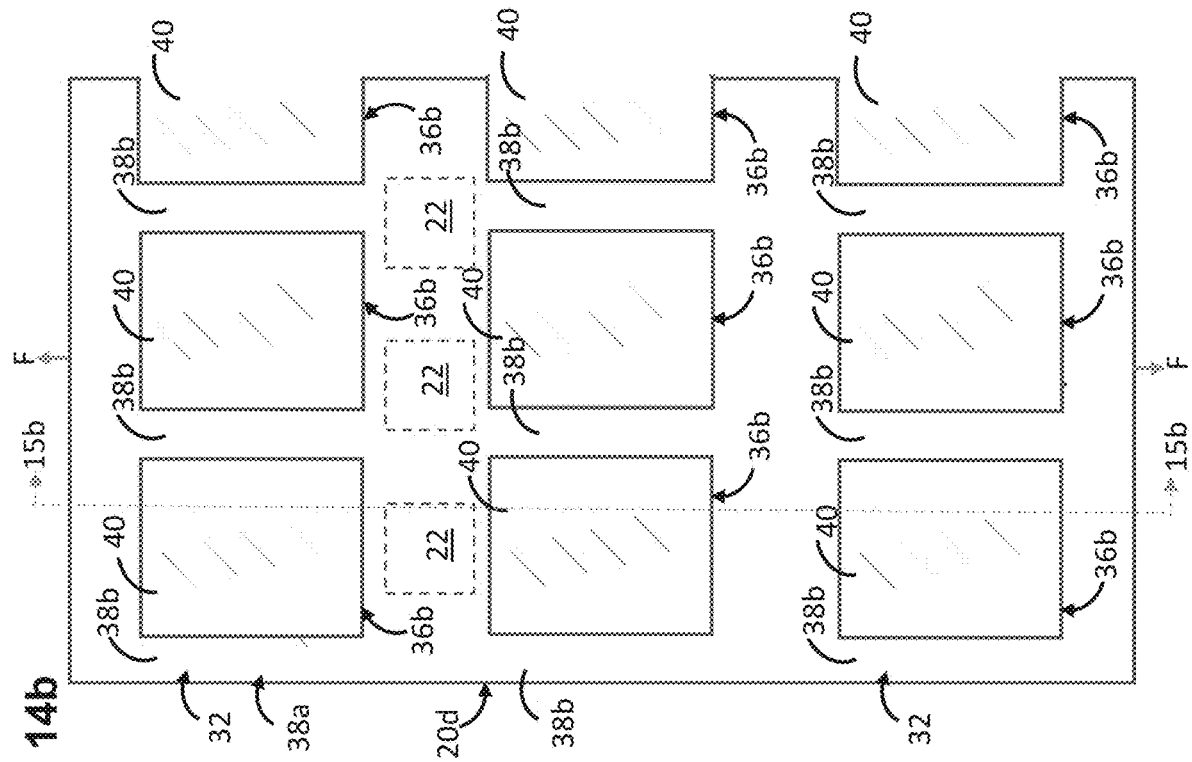
FIG. 14b is a plan view of the relaxed cuff electrode of FIG. 10b in an unrolled form and in the presence of a tensile force.
Figure 14A:
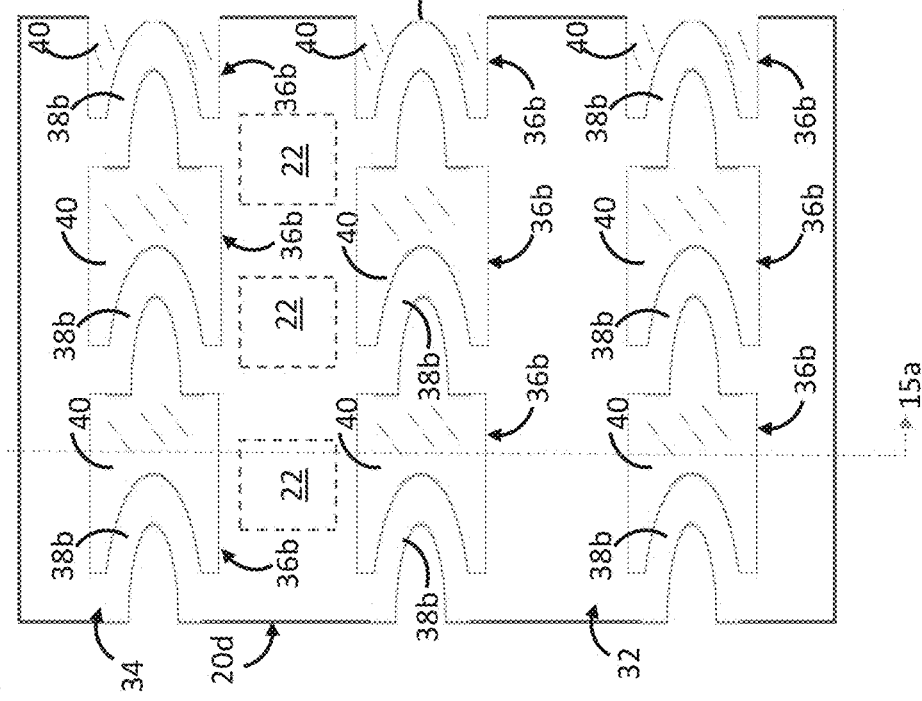
FIG. 14a is a plan view of an alternative embodiment of the cuff electrode of FIG. 10a in an unrolled form and in the absence of a tensile force.

Although the cutouts 36b and corresponding struts 38b are illustrated as being formed only in the first region 32 of the cuff body 20c, it should be appreciated that the cutouts 36b and corresponding struts 38b may be formed in the entirety of a cuff body 20d illustrated in FIGS. 14 and 15. As in the case with the cuff body 20c illustrated in FIGS. 10-13, in the absence of the application of a tensile force F on the cuff body 20d, each strut 38b will be relaxed, as illustrated in FIGS. 14a and 15a, whereas each strut 38b will stretch and tends towards straightening out in response to the application of a tensile force F on the cuff body 20d, as illustrated in FIGS. 14b and 15b. However, because there are three rows of cutouts 36b and corresponding struts 38b in the cuff body 20b, the expandability of the cuff body 20d is further increased relative to the expandability of the cuff body 20c. As with the embodiment illustrated in FIGS. 10-13, a thin stretchable film 40 may be affixed (e.g., via bonding) to the cuff body 20f underneath and completely covering the slits 42 to provide the aforementioned advantages.

In another embodiment illustrated in FIGS. 16-18, a cuff body 20e comprises a plurality of slits 42 within the first region 32 of the cuff body 20e. The plurality of slits 42 are divided into a first set of slits 42a (in this case, one) that extend from a first edge 44a towards a center of the cuff body 20e, and a second set of slits 42b (in this case, one) that extend from a second edge 44b towards the center of the cuff body 20e. The sets of slits 42a, 42b can be staggered in an alternating fashion relative each other, such that the slits 42a, 42b can extend past a centerline 48 between the first and second edge 44a, 44b of the cuff body 20e, thereby maximizing the expandability of the cuff body 20e. The cuff body 20e further comprises a plurality of circular relief cutouts 46 disposed at the ends of the slits 42a, 42b opposite the respective first and second edges 44a, 44b from which the slits 42a, 42b extend. In this manner, expansion of the cuff body 20e will not cause shear forces at the ends of the slits 38a, 38b, which may otherwise rip or tear the cuff body 20e.

In the absence of the application of a tensile force F on the cuff body 20e, each slit 42 will be closed, as illustrated in FIGS. 17a and 18a, whereas each slit 42 will be open and stretched in response to the application of a tensile force F on the cuff body 20e, as illustrated in FIGS. 17b and 18b. Thus, if the cuff body 20e is properly sized to the nerve 26, each slit 42 will close (as shown in FIG. 16a) when the nerve 26 around which the cuff body 20e is circumferentially disposed is not swollen, and each slit 42 will open and stretch (as shown in FIG. 16b) when the nerve 26 around which the cuff body 20e is circumferentially disposed is swollen.

Figure 16A:
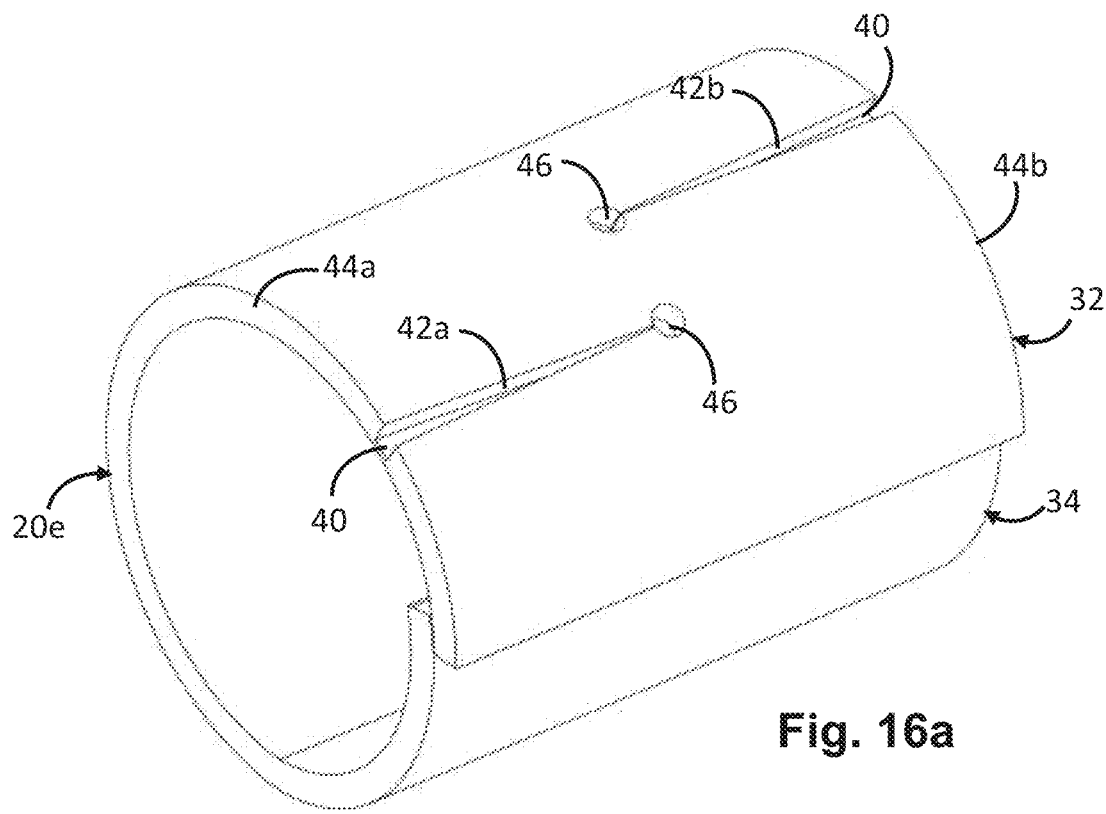
FIG. 16a is a perspective view of still another embodiment of the cuff electrode of the electrode lead of FIG. 1, particularly shown in a rolled-up, relaxed state.
Figure 16B:
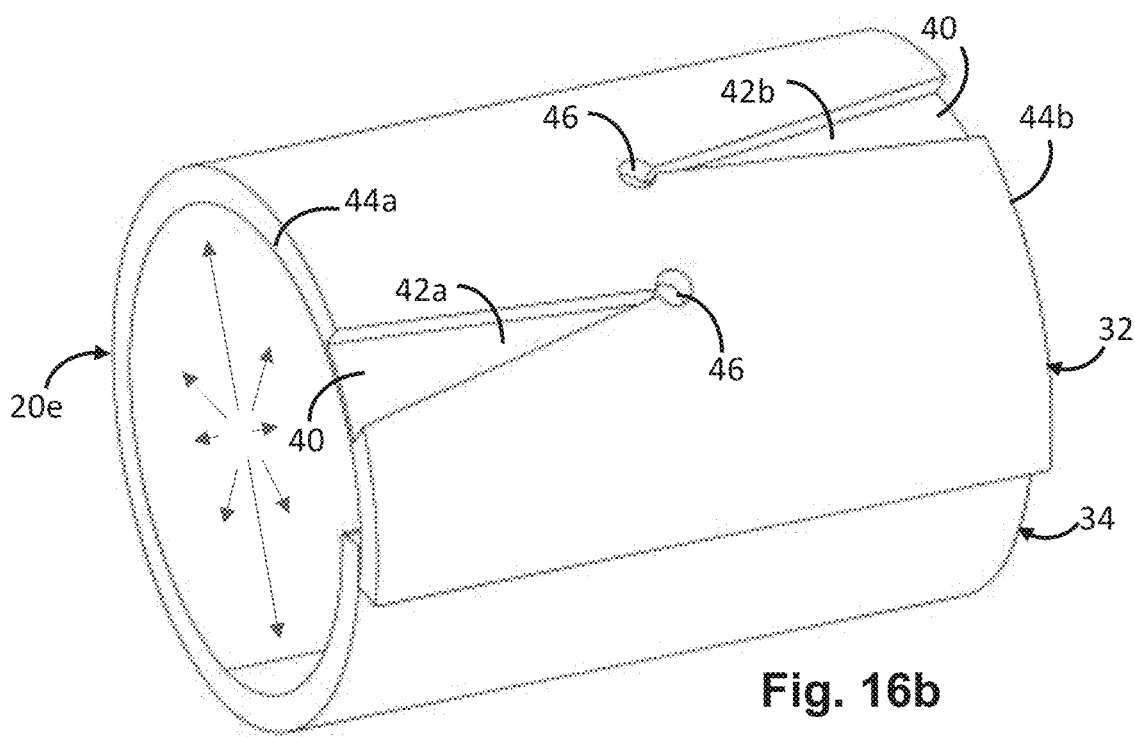
FIG. 16b is a perspective view of the cuff electrode of FIG. 16a, particularly shown in a rolled-up, expanded state.

That is, due to its elastomeric characteristics, when the nerve 26 is not swollen, each slit 42 may be closed (FIGS. 17a and 18a) corresponding to the relaxed state of the cuff body 20e (FIG. 16a). In response to the outward radial force applied to the cuff body 20e by the swelling of the nerve 26, thereby generating a tensile force F, each slit 42 may be open and stretched (FIGS. 17b and 18b), facilitating the transition of the cuff body 20e from its relaxed state (FIG. 16a) to its expanded state (FIG. 16b). In response to the decrease in the outward radial force applied to the cuff body 20e as the swelling of the nerve 26 subsides, thereby diminishing or completely removing the tensile force F, each slit 42 may again close (FIGS. 17a and 18a), facilitating the transition of the cuff body 20e from its expanded state (FIG. 16b) back to its relaxed state (FIG. 16a). Thus, it can be appreciated that the increase in the expandability of the cuff body 20e by the inclusion of the slits 42 prevents, or at least minimizes, the strangling of the nerve 26 as it swells, thereby allowing sufficient flow of blood and other nutrients to the nerve 26. As with the cuff body 20a illustrated in FIGS. 4-7, a thin stretchable film 40 may be affixed (e.g., via bonding) to the cuff body 20e underneath and completely covering the slits 42 to provide the aforementioned advantages.

Although the slits 42 are illustrated as being formed only in the first region 32 of the cuff body 20e, it should be appreciated that the slits 42 may be formed in the entirety of a cuff body 20f illustrated in FIGS. 19 and 20. As in the case with the cuff body 20e illustrated in FIGS. 16-18, in the absence of the application of a tensile force F on the cuff body 20f, each slit 42 will be closed, as illustrated in FIGS. 19a and 20a, whereas each slit 42 will open and stretch in response to the application of a tensile force F on the cuff body 20f, as illustrated in FIGS. 19b and 20b. However, because there are seven slits 42, instead of just two, the expandability of the cuff body 20f is further increased relative to the expandability of the cuff body 20e. As with the embodiment illustrated in FIGS. 16-18, a thin stretchable film 40 may be affixed (e.g., via bonding) to the cuff body 20f underneath and completely covering the slits 42 to provide the aforementioned advantages.

In another embodiment illustrated in FIGS. 21-23, a cuff body 20g comprises a plurality of slits 42 divided into a first set of slits 42a (in this case, two) that extend from a first edge 44a towards the center of the cuff body 20g, a second set of slits 42b (in this case, two) that extend from a second edge 44b towards the center of the cuff body 20g, and a third set of slits 42c that extend through the centerline 48 of the cuff body 20g, but do not extend to the first and second edges 44a, 44b. Rather than being staggered relative to each other in an alternating fashion like the slits 42a, 42b in the cuff body 20e of FIGS. 16-18, which extend past the centerline 48 of the cuff body 20e, the slits 42a, 42b in the cuff body 20g of FIGS. 21-23 are aligned with each other, and do not extend past the centerline 48 of the cuff body 20g. The third set of slits 42c do not extend to the first and second edges 44a, 44b, and can be staggered relative to the first and second sets of slits 42a, 42b in an alternating fashion. Similar to the embodiment illustrated in FIGS. 16-18, the cuff body 20g may further comprise a plurality of circular relief cutouts 46 disposed at the ends of the slits 42a, 42b opposite the respective first and second edge 44a, 44b from which the slits 42a, 42b extend, and both ends of the slits 42c.

Figure 21A:
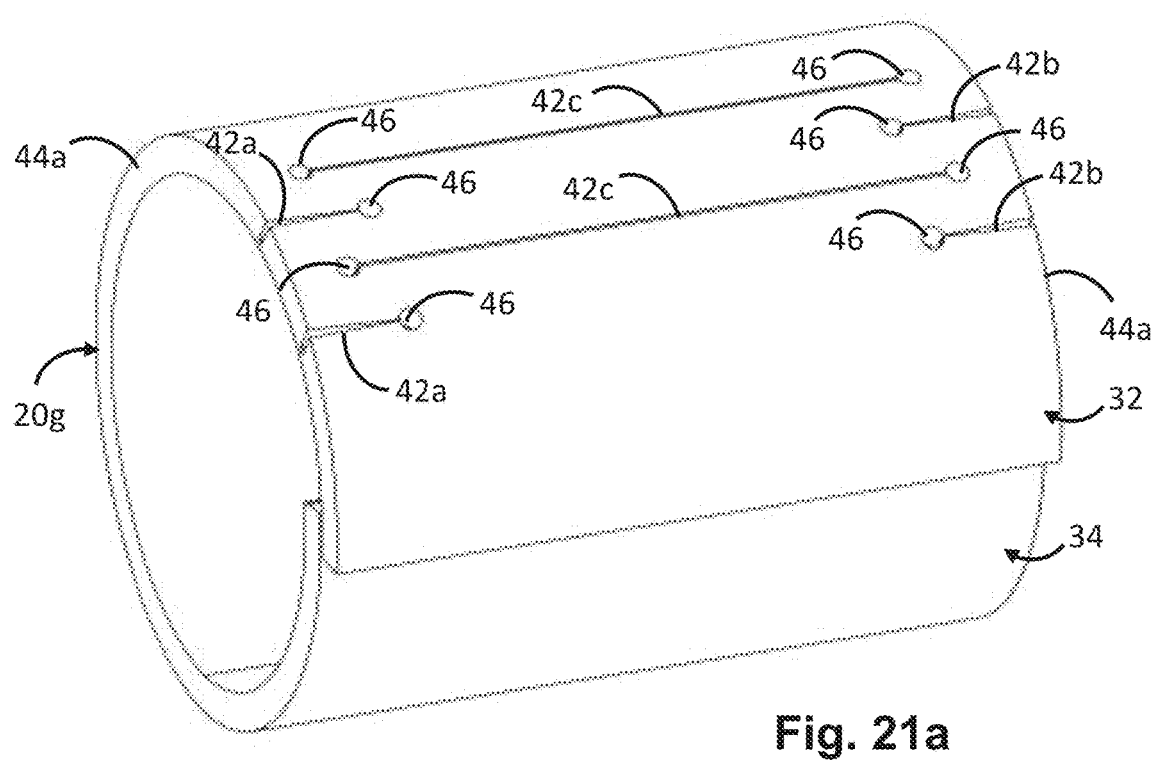
FIG. 21a is a perspective view of yet another embodiment of the cuff electrode of the electrode lead of FIG. 1, particularly shown in a rolled up, relaxed state.
Figure 21B:
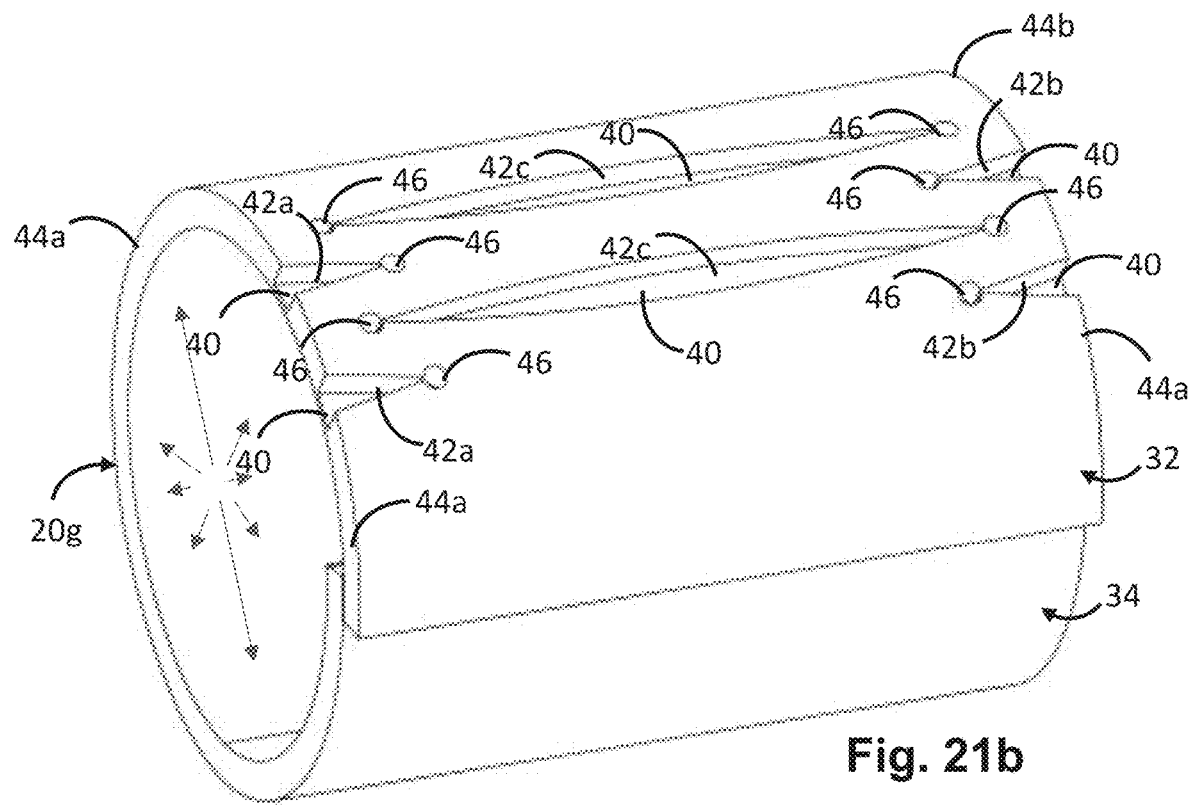
FIG. 21b is a perspective view of the cuff electrode of FIG. 21a, particularly shown in a rolled up, expanded state.
Figure 22A:
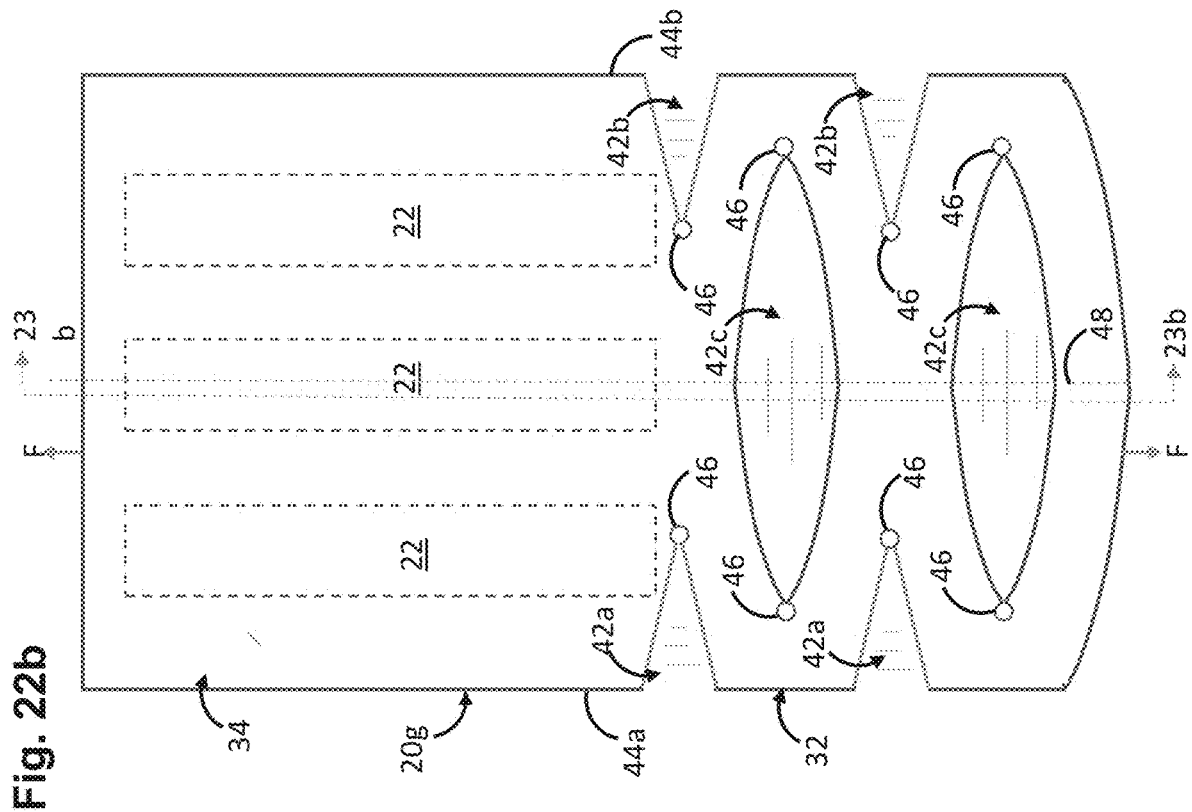
FIG. 22a is a plan view of the relaxed cuff electrode of FIG. 21a in an unrolled form and in the absence of a tensile force.
Figure 22B:
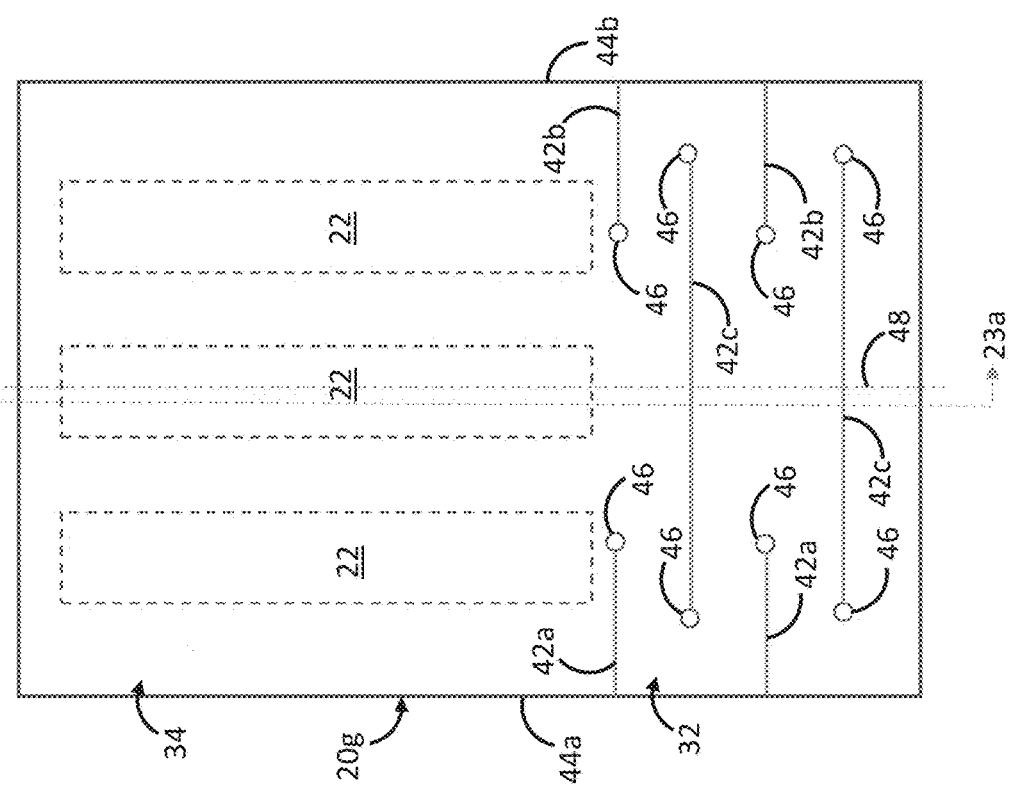
FIG. 22b is a plan view of the expanded cuff electrode of FIG. 21b in an unrolled form and in the presence of a tensile force.
Figure 23A:
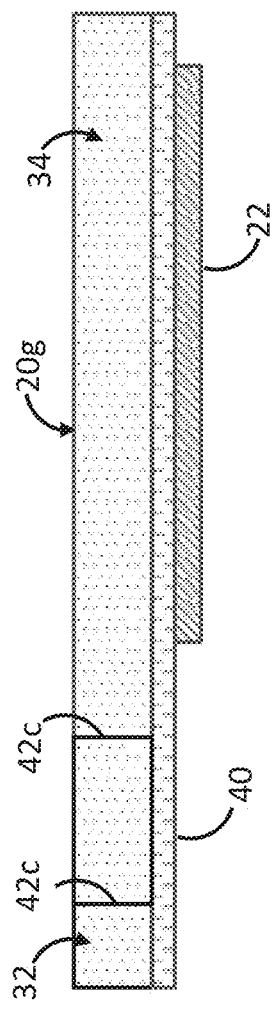
Figure 23B:
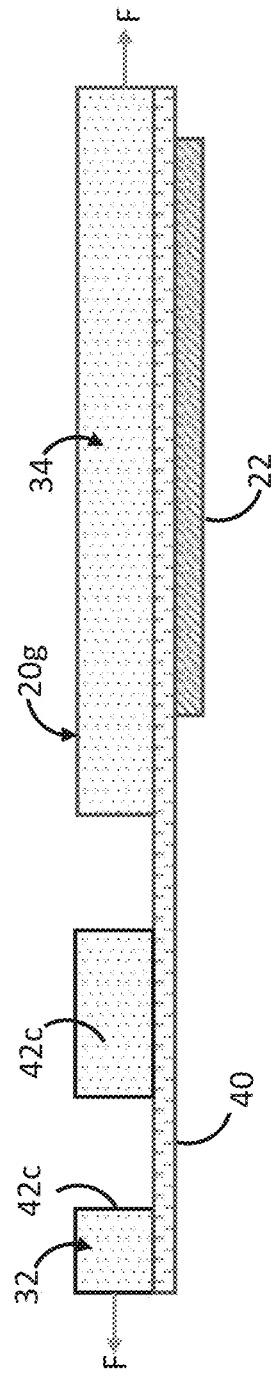
FIG. 23b is a cross-sectional view of the cuff electrode of FIG. 22b, taken along the line 23b-23b.

When there is no tensile force F on the cuff body 20g, each slit 42 will be closed, as illustrated in FIGS. 22a and 23a, whereas each slit 42 will be open and stretched in response to the application of a tensile force F on the cuff body 20g, as illustrated in FIGS. 22b and 23b. Thus, if the cuff body 20g is properly sized to the nerve 26, each slit 42 will close (as shown in FIG. 21a) when the nerve 26 around which the cuff body 20g is circumferentially disposed is not swollen, and will open and stretch (as shown in FIG. 21b) when the nerve 26 around which the cuff body 20g is circumferentially disposed is swollen.

That is, due to its elastomeric characteristics, when the nerve 26 is not swollen, each slit 42 may be closed (FIGS. 22a and 23a) corresponding to the relaxed state of the cuff body 20g (FIG. 21a). In response to the outward radial force applied to the cuff body 20e by the swelling of the nerve 26, thereby generating a tensile force F, each slit 42 may be open and stretched (FIGS. 22b and 23b), facilitating the transition of the cuff body 20g from its relaxed state (FIG. 21a) to its expanded state (FIG. 21b). In response to the decrease in the outward radial force applied to the cuff body 20g as the swelling of the nerve 26 subsides, thereby diminishing or completely removing the tensile force F, each slit 42 may again close (FIGS. 22a and 23a), facilitating the transition of the cuff body 20g from its expanded state (FIG. 21b) back to its relaxed state (FIG. 21a). Thus, it can be appreciated that the increase in the expandability of the cuff body 20g by the inclusion of the slits 42 prevents, or at least minimizes, the strangling of the nerve 26 as it swells, thereby allowing sufficient flow of blood and other nutrients to the nerve 26. As with the cuff body 20a illustrated in FIGS. 16-18, a thin stretchable film 40 may be affixed (e.g., via bonding) to the cuff body 20g underneath and completely covering the slits 42 to provide the aforementioned advantages.

Figure 24B:
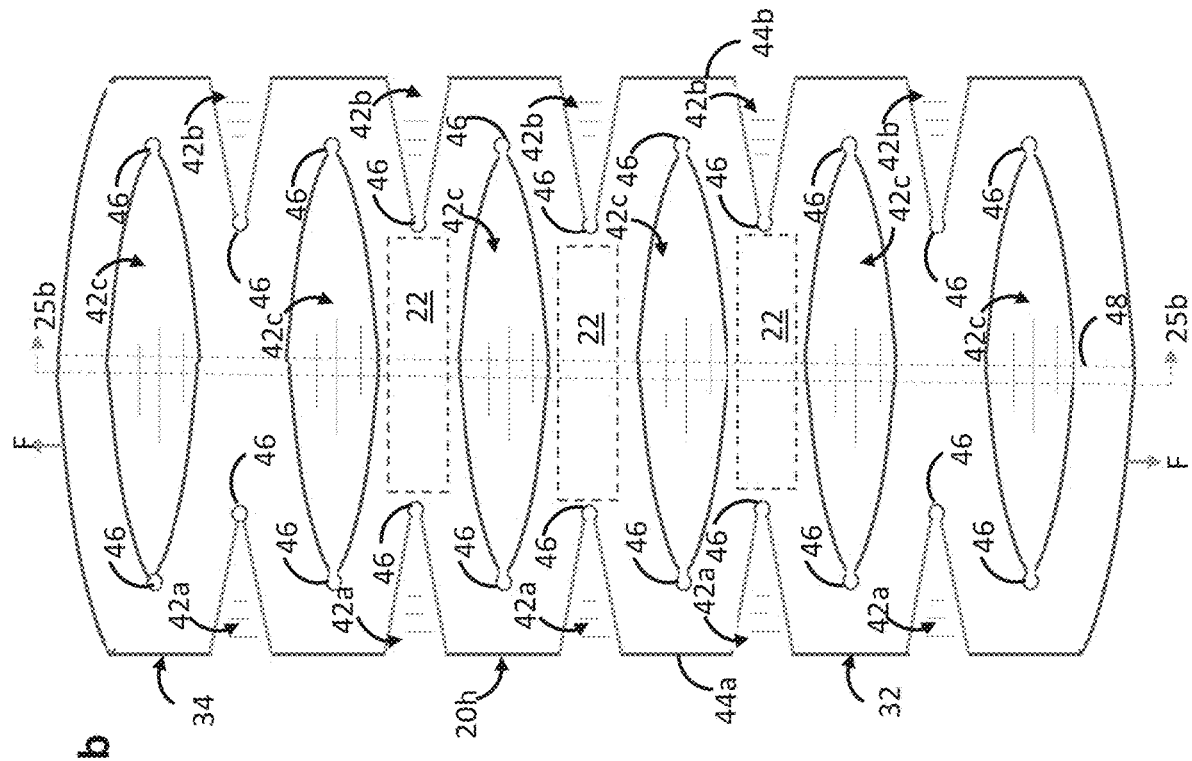
FIG. 24b is a plan view of an alternative embodiment of the relaxed cuff electrode of FIG. 21b in an unrolled form and in the presence of a tensile force.
Figure 24A:
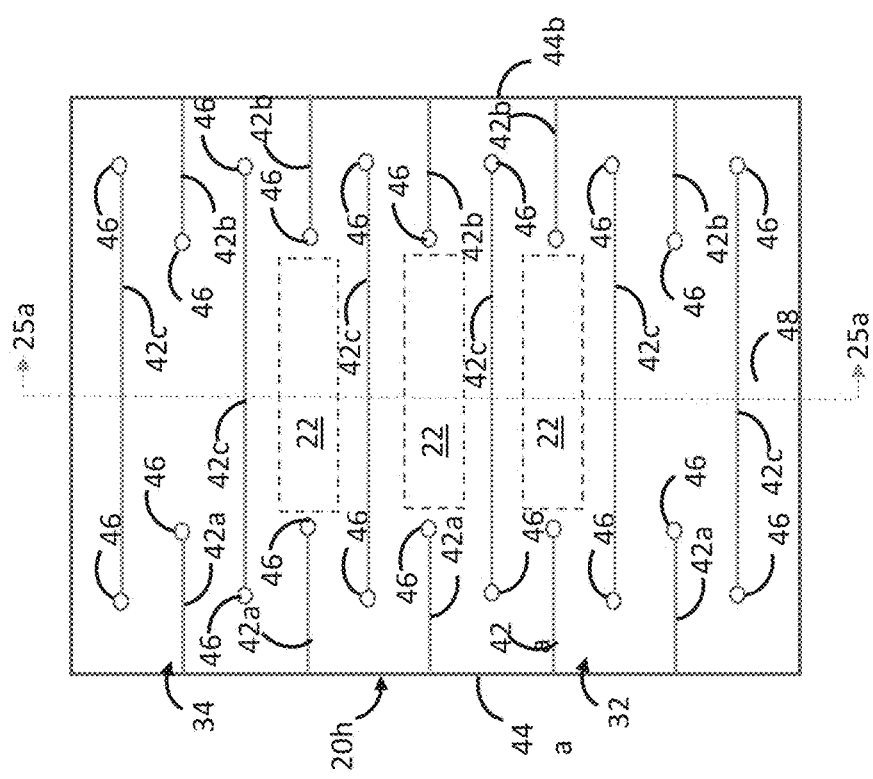
FIG. 24a is a plan view of an alternative embodiment of the relaxed cuff electrode of FIG. 21a in an unrolled form and in the absence of a tensile force.
Figure 25A:
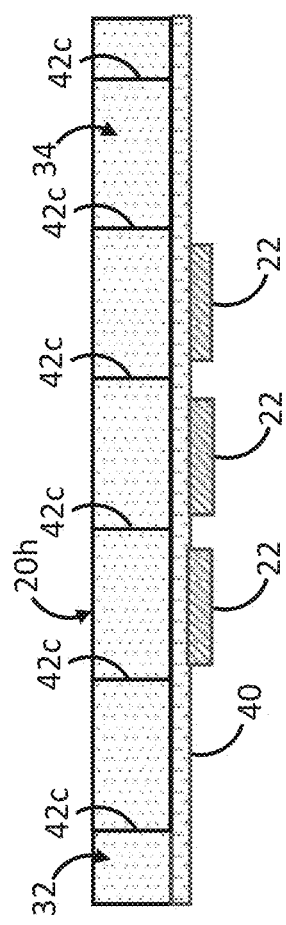
Figure 25B:
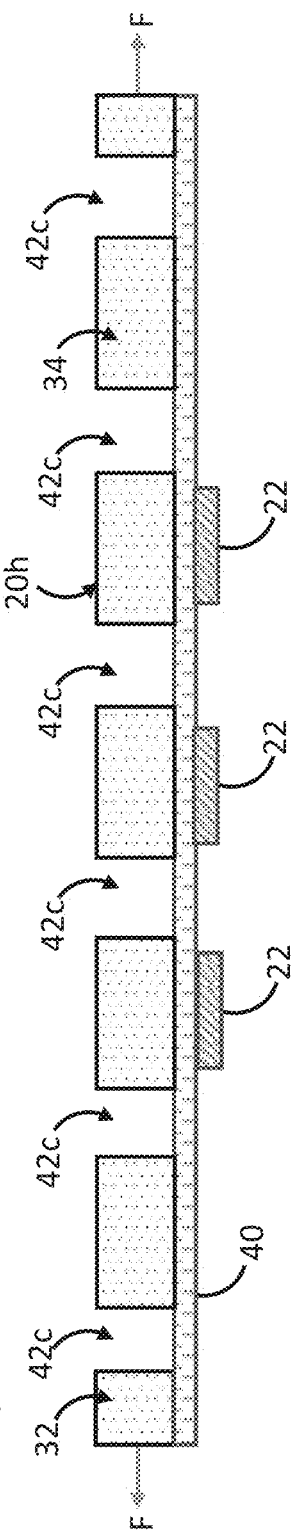
FIG. 25b is a cross-sectional view of the cuff electrode of FIG. 24b, taken along the line 25b-25b.

Although the slits 42 are illustrated as being formed only in the first region 32 of the cuff body 20g, it should be appreciated that the slits 42 may be formed in the entirety of a cuff body 20h illustrated in FIGS. 24 and 25. As in the case with the cuff body 20g illustrated in FIGS. 21-23, when there is no tensile force F on the cuff body 20h, each slit 42 will be closed, as illustrated in FIGS. 24a and 25a, whereas each slit 42 will open and stretch in response to the application of a tensile force F on the cuff body 20h, as illustrated in FIGS. 24b and 25b. However, because there are many more slits, the expandability of the cuff body 20h is further increased relative to the expandability of the cuff body 20g. As with the embodiment illustrated in FIGS. 21-23, a thin stretchable film 40 may be affixed (e.g., via bonding) to the cuff body 20h underneath and completely covering the slits 42 to provide the aforementioned advantages.

In another embodiment illustrated in FIGS. 26-28, a cuff body 20i comprises a wrinkled portion 50a incorporated into the first region 32 of the cuff body 20i and an unwrinkled portion 50b incorporated into the second region 34 of the cuff body 20i. In the illustrated embodiment, the wrinkled portion 50a and the unwrinkled portion 50b have the same thickness.

Figure 28A:
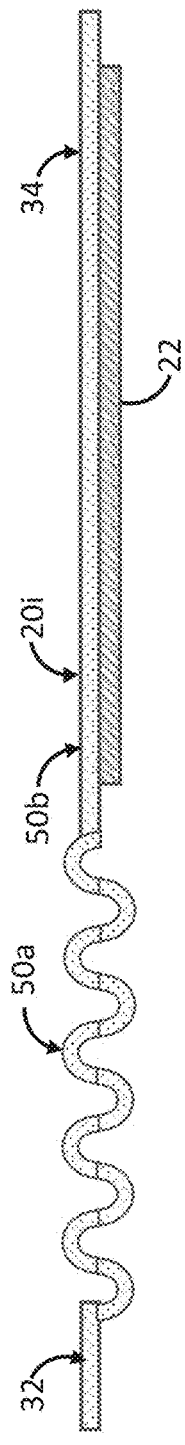
Figure 28B:
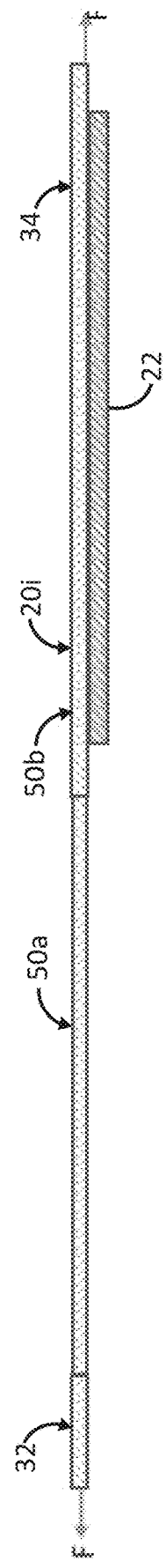
FIG. 28b is a cross-sectional view of the cuff electrode of FIG. 26b, taken along the line 28b-28b.

In the absence of the application of a tensile force F on the cuff body 20i, the wrinkled portion 50a will be furrowed, as illustrated in FIGS. 27a and 28a, whereas the wrinkled portion 50a will be less furrowed and stretch in response to the application of a tensile force F on the cuff body 20i, as illustrated in FIGS. 27b and 28b. Thus, if the cuff body 20i is properly sized to the nerve 26, the wrinkled portion 50a will be more furrowed and contract (as shown in FIG. 26a) when the nerve 26 around which the cuff body 20i is circumferentially disposed is not swollen, and will be less furrowed and stretch (as shown in FIG. 26b) when the nerve 26 around which the cuff body 20i is circumferentially disposed is swollen.

Figure 26A:
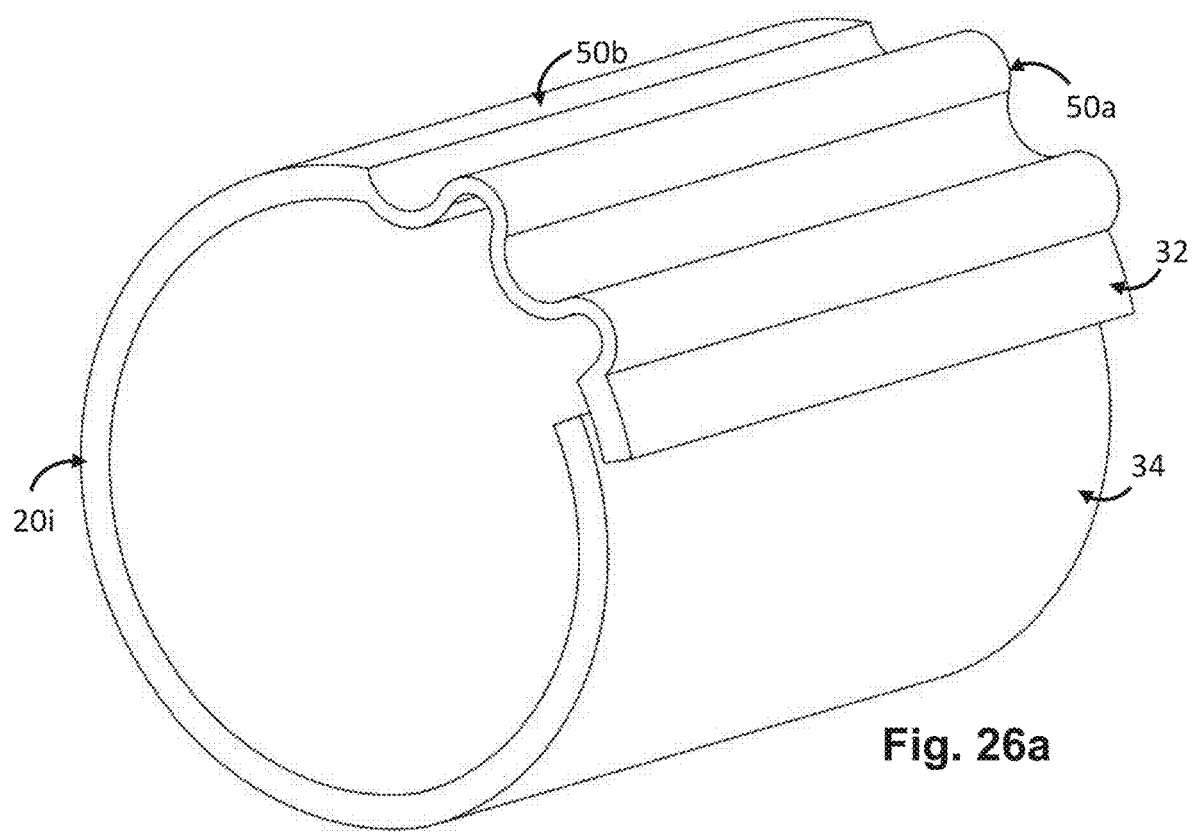
FIG. 26a is a perspective view of yet another embodiment of the cuff electrode of the electrode lead of FIG. 1, particularly shown in a rolled up, relaxed state.
Figure 26B:
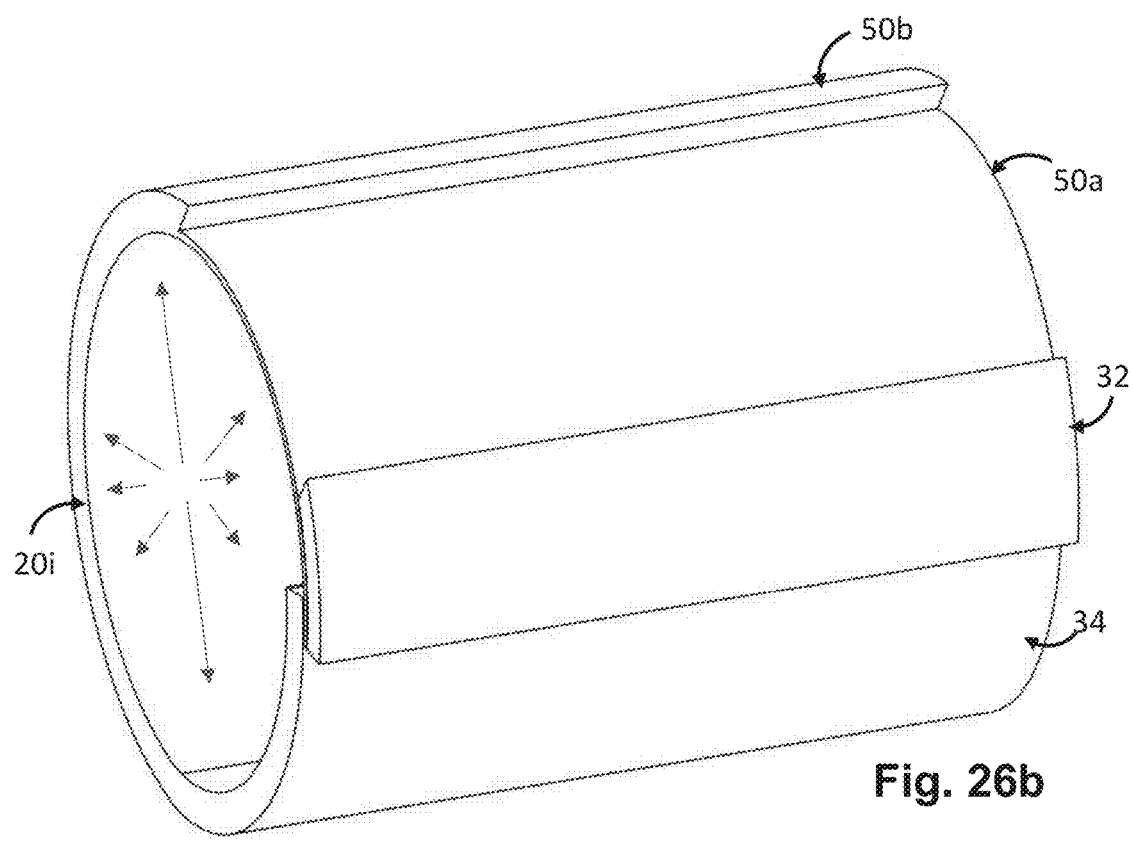
FIG. 26b is a perspective view of the cuff electrode of FIG. 26a, particularly shown in a rolled up, expanded state.

That is, due to its elastomeric characteristics, when the nerve 26 is not swollen, the wrinkled portion 50a may become more furrowed and contract (FIGS. 27a and 28a) corresponding to the relaxed state of the cuff body 20i (FIG. 26a). In response to the outward radial force applied to the cuff body 20i by the swelling of the nerve 26, thereby generating a tensile force F, the wrinkled portion 50a will become less furrowed and stretch (FIGS. 27b and 28b), facilitating the transition of the cuff body 20i from its relaxed state (FIG. 26a) to its expanded state (FIG. 26b). In response to the decrease in the outward radial force applied to the cuff body 20i as the swelling of the nerve 26 subsides, thereby diminishing or completely removing the tensile force F, the wrinkled portion 50a may again become more furrowed and contract (FIGS. 27a and 28a), facilitating the transition of the cuff body 20i from its expanded state (FIG. 26b) back to its relaxed state (FIG. 26a). Thus, it can be appreciated that the increase in the expandability of the cuff body 20i by the inclusion of the wrinkled portion 50a prevents, or at least minimizes, the strangling of the nerve 26 as it swells, thereby allowing sufficient flow of blood and other nutrients to the nerve 26.

In another embodiment illustrated in FIGS. 29-31, a cuff body 20j comprises a thinner stretchable portion 52a incorporated into the first region 32 of the cuff body 20j and a thicker portion 52b incorporated into the second region 34 of the cuff body 20j.

Figure 29A:
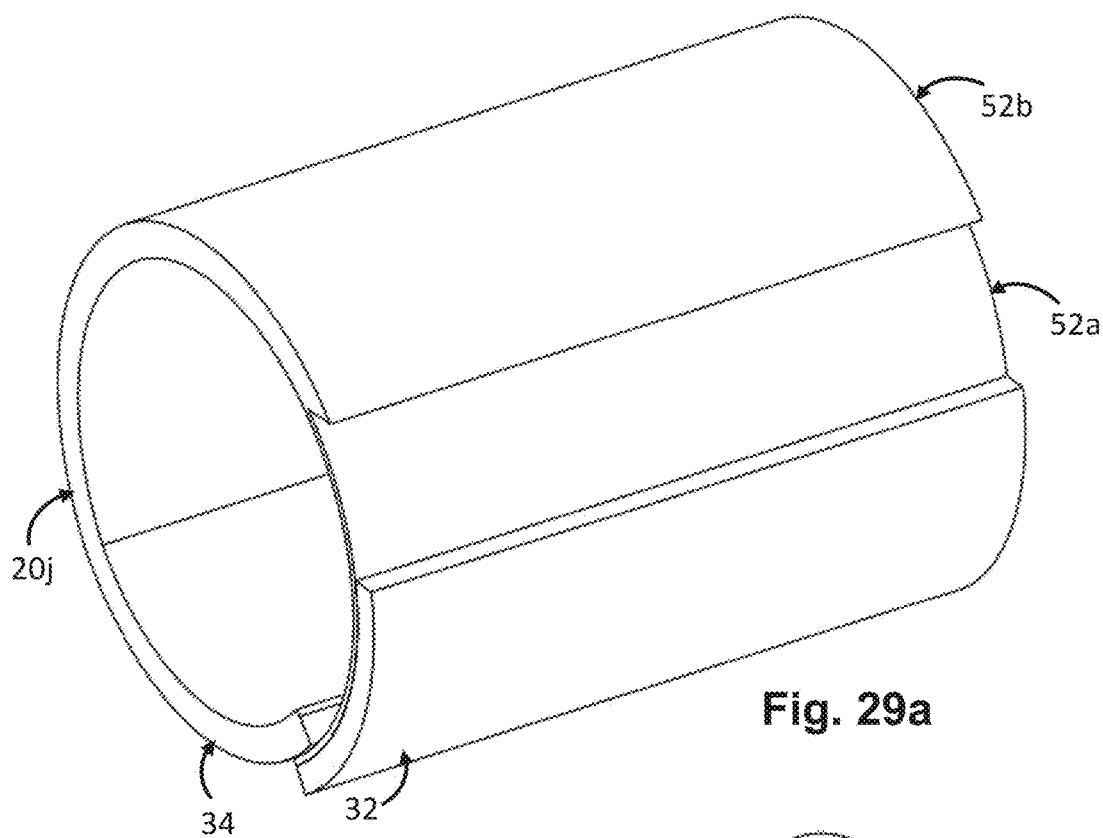
FIG. 29a is a perspective view of yet another embodiment of the cuff electrode of the electrode lead of FIG. 1, particularly shown in a rolled up, relaxed state.
Figure 29B:
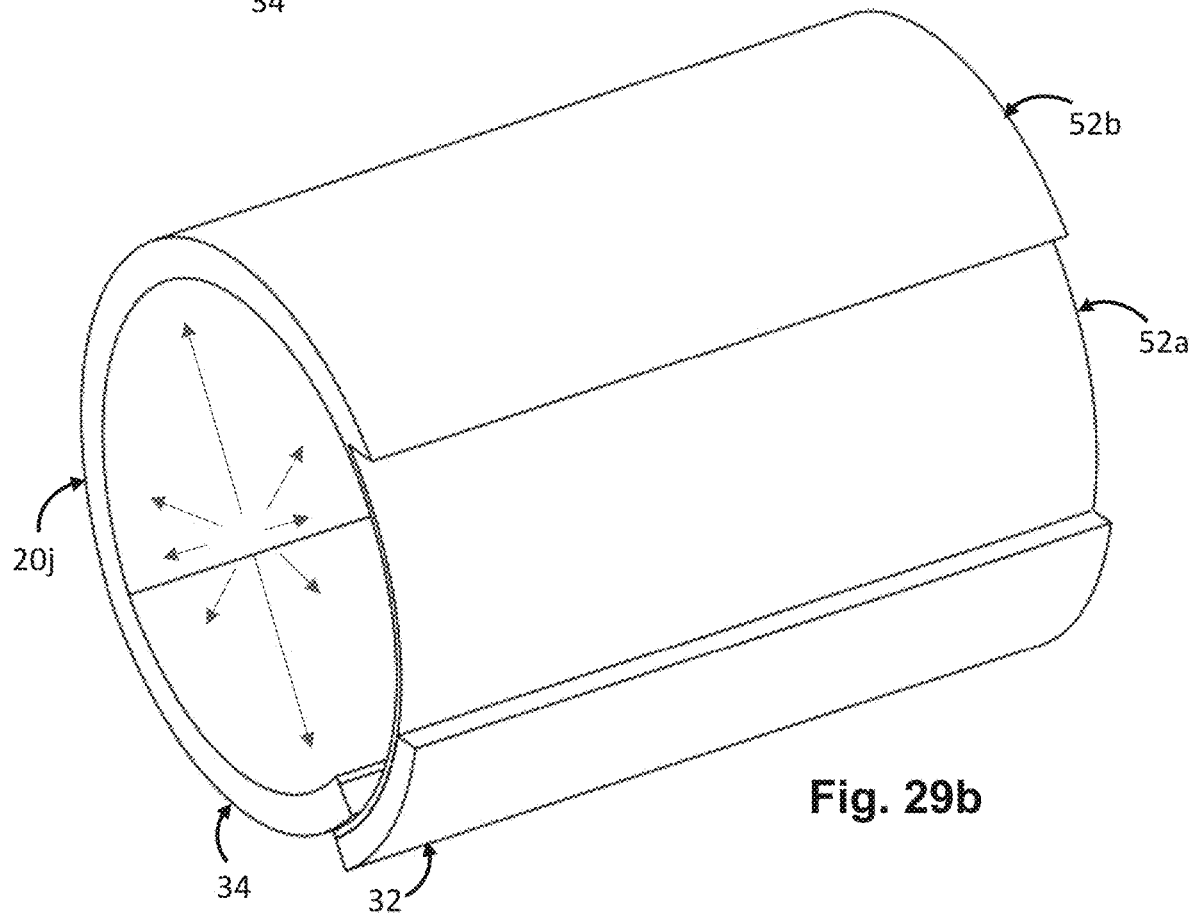
FIG. 29b is a perspective view of the cuff electrode of FIG. 29a, particularly shown in a rolled-up, expanded state.
Figure 30B:
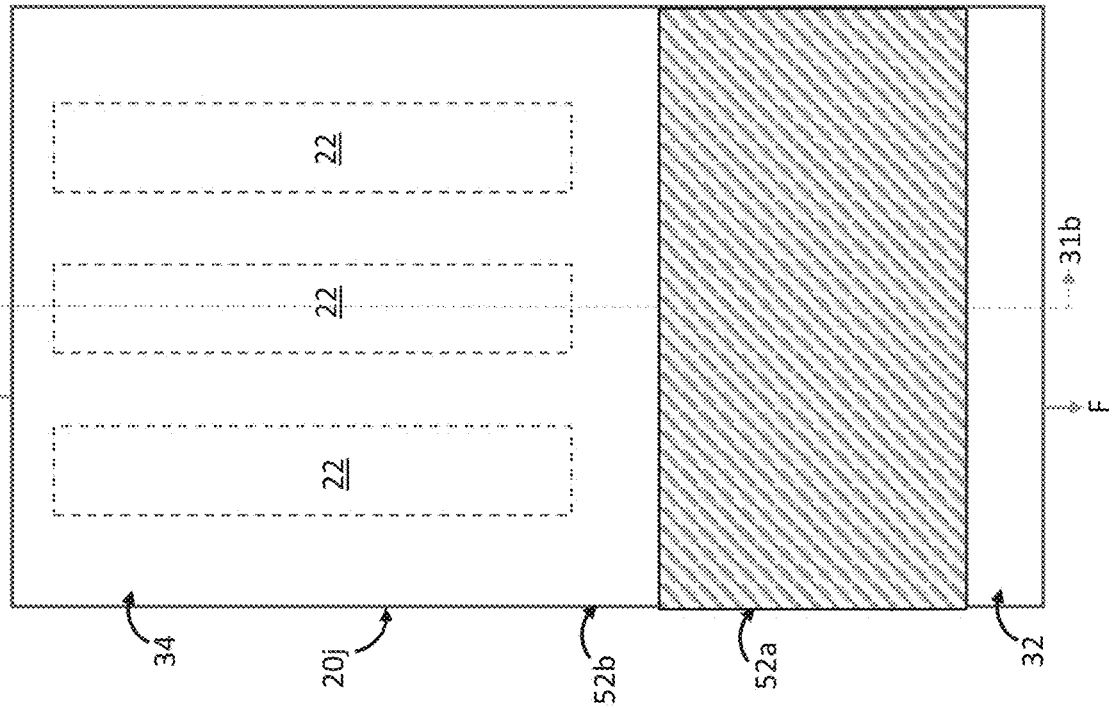
FIG. 30b is a plan view of the expanded cuff electrode of FIG. 29b in an unrolled form and in the presence of a tensile force.
Figure 30A:
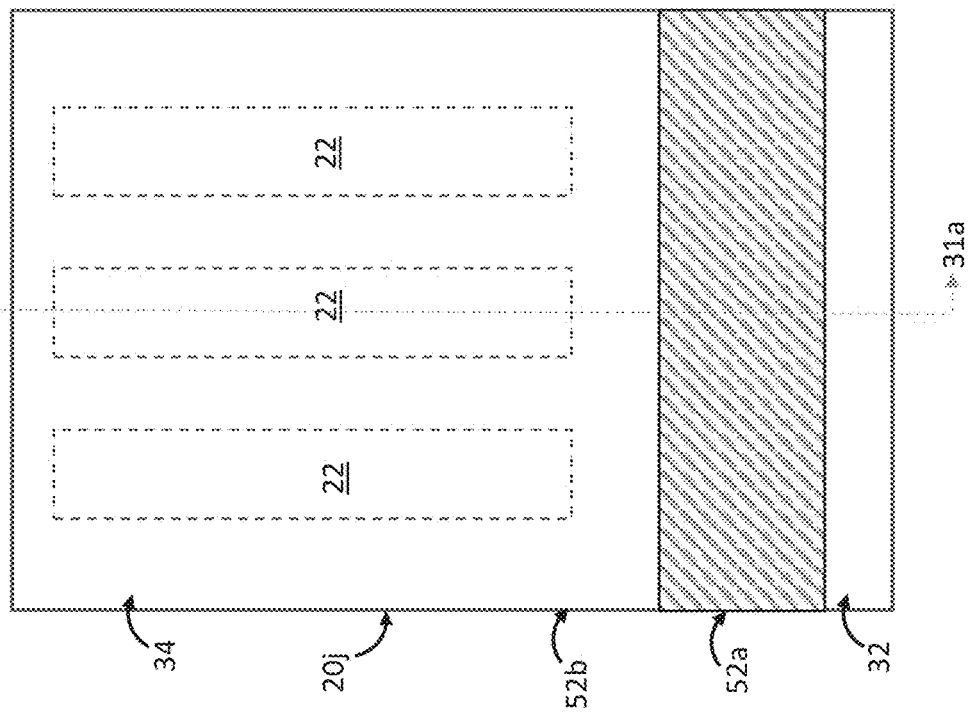
FIG. 30a is a plan view of the relaxed cuff electrode of FIG. 29a in an unrolled form and in the absence of a tensile force.
Figure 31A:
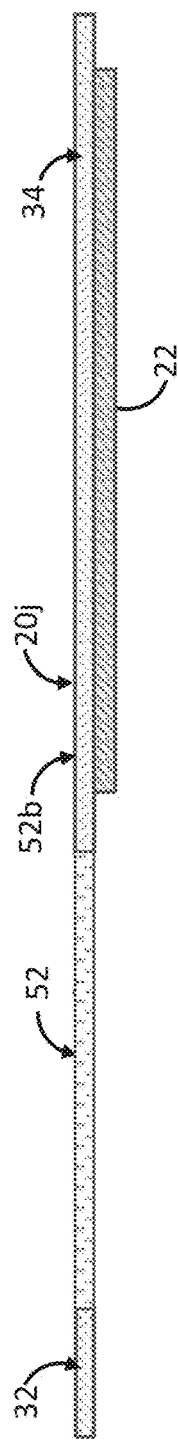
Figure 31B:
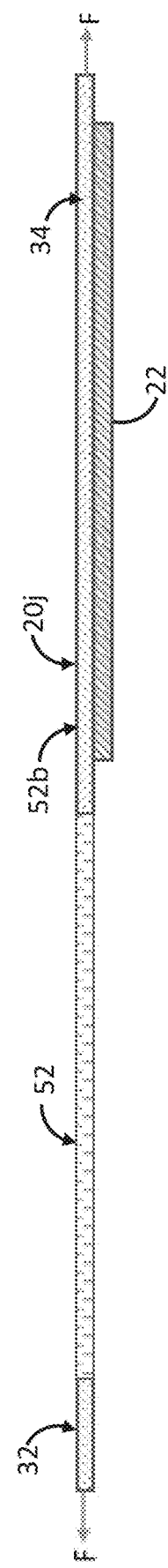
FIG. 31b is a cross-sectional view of the cuff electrode of FIG. 29b, taken along the line 31b-31b.

In the absence of the application of a tensile force F on the cuff body 20j, the stretchable portion 52a will relax, as illustrated in FIGS. 30a and 31a, whereas the stretchable portion 52a will stretch in response to the application of a tensile force F on the cuff body 20j, as illustrated in FIGS. 30b and 31b. Thus, if the cuff body 20j is properly sized to the nerve 26, the stretchable portion 52a will relax (as shown in FIG. 29a) when the nerve 26 around which the cuff body 20j is circumferentially disposed is not swollen, and will stretch (as shown in FIG. 29b) when the nerve 26 around which the cuff body 20j is circumferentially disposed is swollen.

That is, due to its elastomeric characteristics, when the nerve 26 is not swollen, the stretchable portion 52a will be relaxed (FIGS. 30a and 31a) corresponding to the relaxed state of the cuff body 20j (FIG. 29a). In response to the outward radial force applied to the cuff body 20j by the swelling of the nerve 26, thereby generating a tensile force F, the stretchable portion 52a will stretch (FIGS. 30b and 31b), facilitating the transition of the cuff body 20j from its relaxed state (FIG. 29a) to its expanded state (FIG. 29b). In response to the decrease in the outward radial force applied to the cuff body 20j as the swelling of the nerve 26 subsides, thereby diminishing or completely removing the tensile force F, the stretchable portion 52a may again relax (FIGS. 30a and 31a), facilitating the transition of the cuff body 20j from its expanded state (FIG. 29b) back to its relaxed state (FIG. 29a). Thus, it can be appreciated that the increase in expandability of the cuff body 20j by the inclusion of the stretchable portion 52a prevents, or at least minimizes, the strangling of the nerve 26 as it swells, thereby allowing sufficient flow of blood and other nutrients to the nerve 26.

Figure 32A:
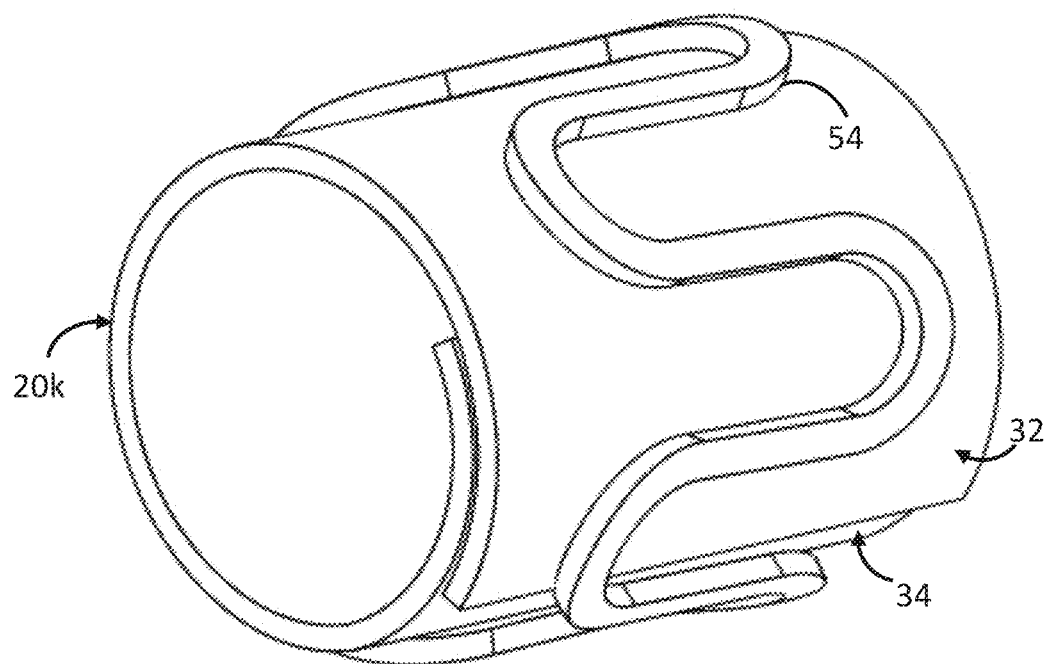
FIG. 32a is a perspective view of yet another embodiment of the cuff electrode of the electrode lead of FIG. 1, particularly shown in a rolled-up, relaxed state.
Figure 32B:
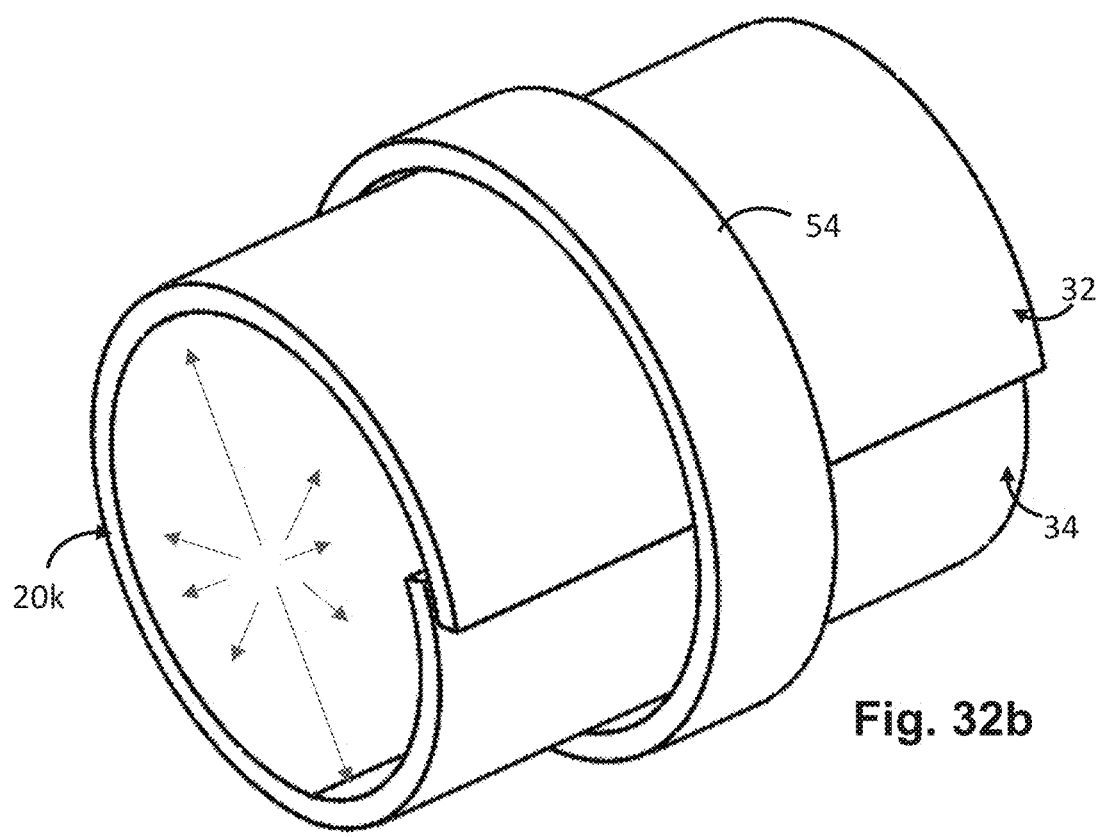
FIG. 32b is a perspective view of the cuff electrode of FIG. 32a, particularly shown in a rolled-up, expanded state.
Figure 33B:
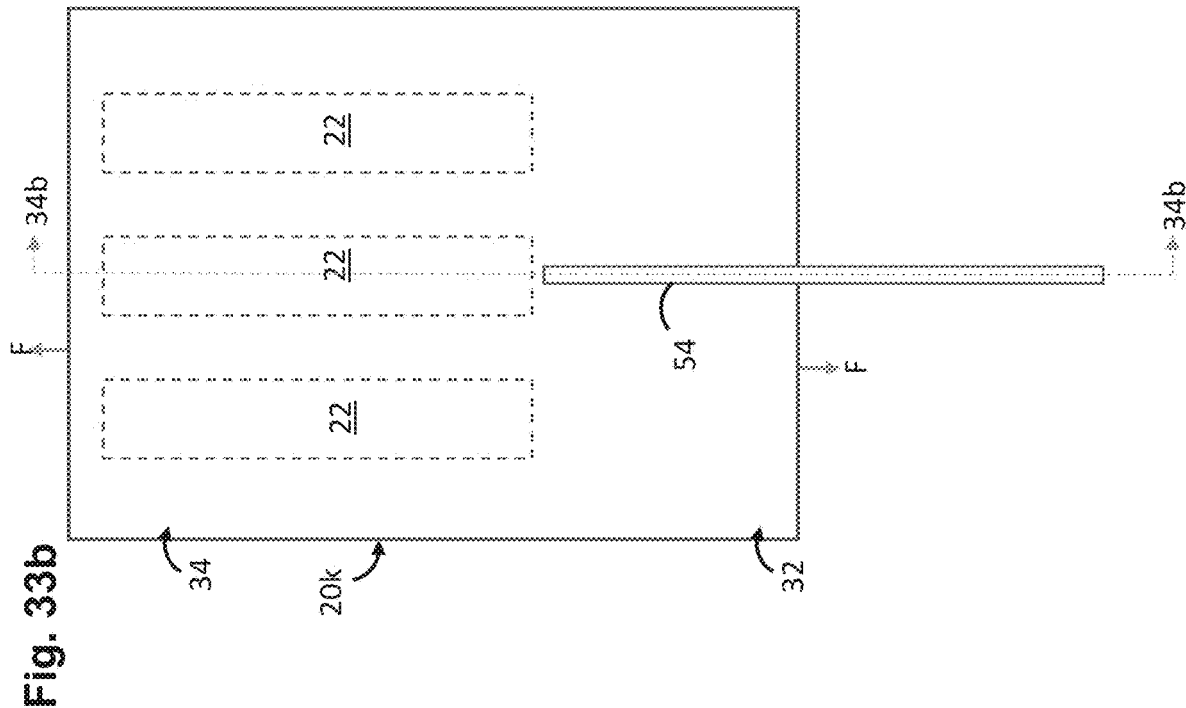
FIG. 33b is a plan view of the expanded cuff electrode of FIG. 32b in an unrolled form and in the presence of a tensile force.
Figure 33A:
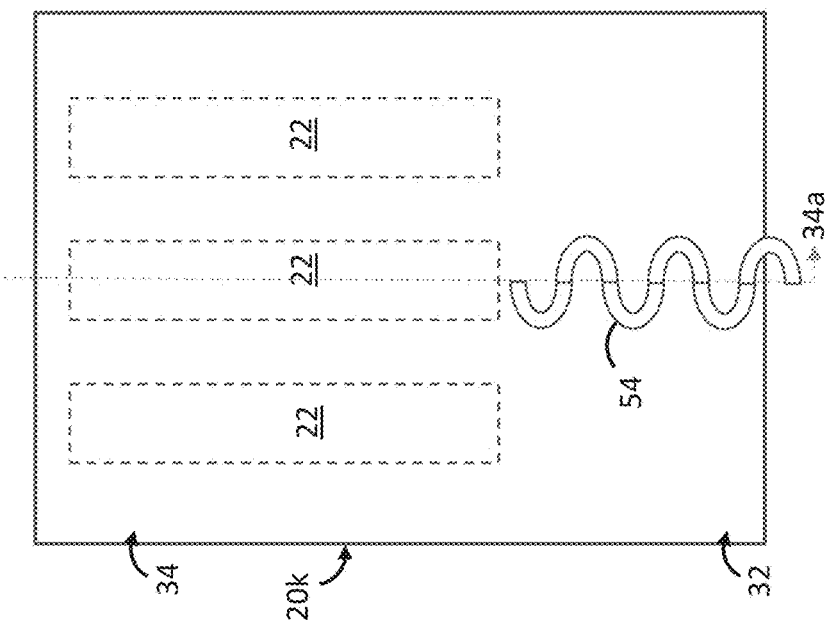
FIG. 33a is a plan view of the relaxed cuff electrode of FIG. 32a in an unrolled form and in the absence of a tensile force.
Figure 34A:
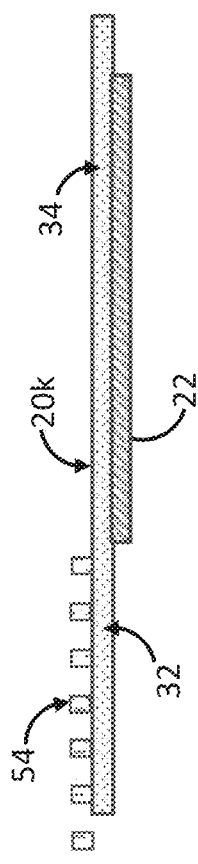
Figure 34B:
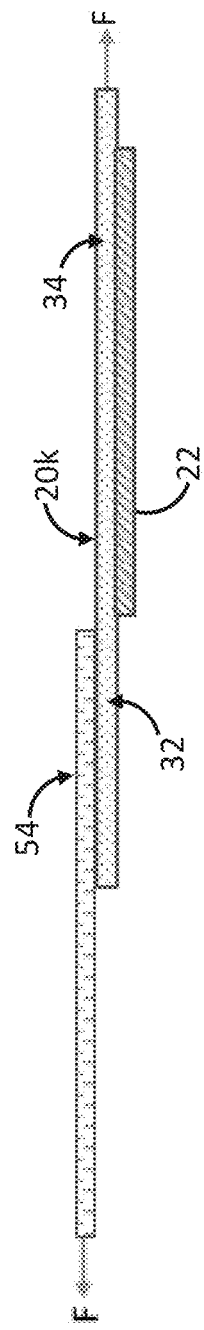
FIG. 34b is a cross-sectional view of the cuff electrode of FIG. 32b, taken along the line 34b-34b.

In another embodiment illustrated in FIGS. 32-34, a cuff body 20k comprises a serpentine strap 54 extending from the first region 32 of the cuff body 20k and configured for being affixed to the second region 34 of the cuff body 20k. When there is no tensile force F on the cuff body 20k, the serpentine strap 54 will relax, as illustrated in FIGS. 33a and 34a, whereas the serpentine strap 54 will stretch in response to the application of a tensile force F on the cuff body 20k, as illustrated in FIGS. 33b and 34b. Thus, if the cuff body 20k is properly sized to the nerve 26, the serpentine strap 54 will relax (as shown in FIG. 32a) when the nerve 26 around which the cuff body 20k is circumferentially disposed is not swollen, and will stretch (as shown in FIG. 32b) when the nerve 26 around which the cuff body 20k is circumferentially disposed is swollen.

That is, due to its elastomeric characteristics, when the nerve 26 is not swollen, the serpentine strap 54 will be relaxed (FIGS. 33a and 33a) corresponding to the relaxed state of the cuff body 20k (FIG. 32a). In response to the outward radial force applied to the cuff body 20k by the swelling of the nerve 26, thereby generating a tensile force F, the serpentine 54 will stretch (FIGS. 33b and 34b), facilitating the transition of the cuff body 20k from its relaxed state (FIG. 32a) to its expanded state (FIG. 32b). In response to the decrease in the outward radial force applied to the cuff body 20k as the swelling of the nerve 26 subsides, thereby diminishing or completely removing the tensile force F, the serpentine strap 54 may again relax (FIGS. 33a and 34a), facilitating the transition of the cuff body 20k from its expanded state (FIG. 32b) back to its relaxed state (FIG. 32a). Thus, it can be appreciated that the increase in the expandability of the cuff body 20k by the inclusion of the serpentine strap 54 prevents, or at least minimizes, the strangling of the nerve 26 as it swells, thereby allowing sufficient flow of blood and other nutrients to the nerve 26.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An electrode lead, comprising:
   an elongated lead body having a proximal end and a distal end;
   at least one lead connector terminal affixed to the proximal end of the lead body;
   a biologically compatible, elastic, electrically insulative cuff body affixed to the distal end of the lead body, the cuff body configured for being circumferentially disposed around a nerve, the cuff body comprising first and second opposing regions and first and second opposing axially spaced circumferential edges when disposed around the nerve, a serpentine strap extending from the first region cuff body, the serpentine strap configured for being affixed to the second region of the cuff body, such that the serpentine strap alternately meanders toward and away from each of the first and second axially spaced circumferential edges when the cuff body is in a relaxed state when disposed around the nerve, the serpentine strap configured for becoming less serpentine in response to an increase in an outward radial force applied to the cuff body by a swelling of the nerve, thereby facilitating the transition of the cuff body from the relaxed state to an expanded state when disposed around the nerve;
   at least one electrode contact affixed to the cuff body; and
   at least one electrical conductor extending through the lead body between the at least one lead connector terminal and the at least one electrode contact.

2. The electrode lead of claim 1, wherein the cuff body is composed of silicone.

3. The electrode lead of claim 1, wherein the cuff body has a thickness less than 1 mm.

4. The electrode lead of claim 1, wherein the at least one electrode contact is configured for being on an inner surface of the cuff body when disposed around the nerve.

5. The electrode lead of claim 1, further comprising a locking feature configured for firmly securing the cuff body around the nerve.

6. The electrode lead of claim 1, wherein the serpentine strap is configured for becoming more serpentine in response to a decrease in the outward radial force applied to the cuff body as the swelling of the nerve subsides, thereby facilitating the transition of the cuff body from the expanded state back to the relaxed state when disposed around the nerve.

7. The electrode lead of claim 6, wherein, when the cuff body is configured for being circumferentially disposed around the nerve, the serpentine strap has a planar shape with a thickness extending along a radius of the nerve, and a width extending along a length of the nerve, the width being greater than the thickness, such that the width of the serpentine strap meanders between the axially spaced circumferential edges of the cuff body when the cuff body is in the relaxed state.

8. The electrode lead of claim 7, wherein the thickness of the serpentine strap does not meander along a radius of the cuff body when the cuff body in the relaxed state.

9. The electrode lead of claim 6, wherein the serpentine strap meanders between the first and second edges across a centerline of the serpentine strap between the first and second axially spaced circumferential edges.

* * * * *